United States Patent
Turner

(10) Patent No.: US 9,562,253 B1
(45) Date of Patent: Feb. 7, 2017

(54) DISTINGUISHING BETWEEN A BACTERIAL AND NON-BACTERIAL INFECTION AT THE POINT OF CARE

(71) Applicant: Point of Care Technologies, LLC, Greenville, SC (US)

(72) Inventor: Ronald Turner, Greenville, SC (US)

(73) Assignee: POINT OF CARE DIAGNOSTICS, LLC, Greenville, SC (US)

( * ) Notice: Subject to any disclaimer, the term of this patent is extended or adjusted under 35 U.S.C. 154(b) by 77 days.

(21) Appl. No.: 14/319,305

(22) Filed: Jun. 30, 2014

Related U.S. Application Data

(62) Division of application No. 13/673,615, filed on Nov. 9, 2012, now abandoned.

(51) Int. Cl.
- *G01N 31/22* (2006.01)
- *C12Q 1/04* (2006.01)
- *C12Q 1/32* (2006.01)
- *C12Q 1/48* (2006.01)

(52) U.S. Cl.
CPC . *C12Q 1/04* (2013.01); *C12Q 1/32* (2013.01); *C12Q 1/485* (2013.01)

(58) Field of Classification Search
CPC .............. C12Q 1/04; C12Q 1/32; C12Q 1/485
See application file for complete search history.

(56) References Cited

U.S. PATENT DOCUMENTS

| | | | |
|---|---|---|---|
| 3,745,090 A | 7/1973 | Chappelle et al. | |
| 4,014,745 A | 3/1977 | Fletcher et al. | |
| 4,132,599 A | 1/1979 | Fletcher et al. | |
| 4,303,752 A | 12/1981 | Kolehmainen et al. | |
| 4,704,355 A | 11/1987 | Bernstein | |

(Continued)

FOREIGN PATENT DOCUMENTS

| | | |
|---|---|---|
| EP | 0299601 | 1/1989 |
| GB | 2059990 | 4/1981 |

(Continued)

OTHER PUBLICATIONS

Wikipedia; "ATP Synthase", http://en.wikipedia.org/wiki/atp_synthase; 10 pages, print date: Jul. 24, 2014.

(Continued)

*Primary Examiner* — Dennis M White
(74) *Attorney, Agent, or Firm* — Richard A. Brisbin, Esq.; Jeffrey T. Stover, Esq.; Haynsworth Sinkler Boyd, P.A.

(57) ABSTRACT

A method includes obtaining a sample from a patient; applying, to the sample, a reagent to cause bacterial cells to release adenosine triphosphate (ATP) when the sample includes the bacterial cells; applying another reagent that reacts with the ATP to form a colorimetric agent; detecting whether the sample changes in appearance as observed by an unaided eye of a practitioner when a concentration of the agent is greater than a threshold; identifying a time period from when the other reagent is applied to when the change in appearance is detected; and determines a severity, of a bacterial infection, based on the time period. The severity corresponds to a severity level when the time period is less than a duration of a point of care visit by a first amount, or a higher severity level when the time period is less than the duration by more than the first amount.

22 Claims, 16 Drawing Sheets

(56) References Cited

U.S. PATENT DOCUMENTS

| | | | |
|---|---|---|---|
| 5,169,789 | A | 12/1992 | Bernstein |
| 5,624,810 | A | 4/1997 | Miller et al. |
| 5,888,725 | A | 3/1999 | Sanders |
| 5,908,751 | A | 6/1999 | Higo et al. |
| 5,916,802 | A | 6/1999 | Andreotti |
| 5,965,453 | A * | 10/1999 | Skiffington ............ B01L 3/502 422/52 |
| 6,458,547 | B1 | 10/2002 | Bryan et al. |
| 6,887,681 | B2 | 5/2005 | DiCesare et al. |
| 7,422,868 | B2 | 9/2008 | Fan et al. |
| 7,757,635 | B2 | 7/2010 | Fullam et al. |
| 8,512,970 | B2 | 8/2013 | Sutton et al. |
| 2004/0142401 | A1* | 7/2004 | Iwata ................... C12Q 1/008 435/14 |
| 2004/0197845 | A1 | 10/2004 | Hassibi et al. |
| 2006/0008860 | A1 | 1/2006 | Fan et al. |
| 2011/0136106 | A1 | 6/2011 | Schramm |
| 2012/0245128 | A1 | 9/2012 | Haag et al. |
| 2012/0321570 | A1 | 12/2012 | Kutsch et al. |
| 2013/0084588 | A1 | 4/2013 | Ericson et al. |

FOREIGN PATENT DOCUMENTS

| | | |
|---|---|---|
| GB | WO9514105 | 5/1995 |
| GB | WO0008203 | 2/2000 |
| GB | WO0104345 | 1/2001 |
| GB | WO2004090089 | 10/2004 |
| SE | WO8902929 | 4/1989 |
| WO | WO8807584 | 10/1988 |
| WO | WO9216648 | 10/1992 |
| WO | WO2013130875 | 9/2013 |

OTHER PUBLICATIONS

Wikipedia; "Bacterial Cell Structure", http://en.wikipedia.org/wiki/bacterial_cell_structure; 11 pages, print date: Jul. 24, 2014.

New Horizons Diagnostics; "Profile®—1 Rapid Bacterial Detection" Bioluminometer Model 3560; 25 pages, Print date: Dec. 7, 2012.

Hygiena, LLC; SystemSURE Plus ATP Hygiene Monitoring System; 3 pages, Print date: Dec. 7, 2012.

Wikipedia; "Adenosine triphosphate", http://en.wikipedia.org/wiki/Adenosine_triphosphate; 15 pages; print date: Jul. 24, 2014.

Cariscreen; "Cariscreen Caries Susceptibility Testing Meter"; http://carifree.com/dentist/cariscreen-caries-susceptibility-testing-meter.html; 2 pages; print date: Jul. 24, 2014.

Vesna Ivancic, et al; "Rapid Antimicrobial Susceptibility Determination of Uropathogens in Clinical Urine Specimens by Use of ATP Bioluminescence"; Journal of Clinical Microbiology; vol. 46, No. 4; Apr. 2008; pp. 1213-1219.

EMD Millipore; "Milliflex® Rapid Microbiology Detection and Enumeration System for Bioburden Testing"; https://www.millipore.com/catalogue/module/C107111; 3 pages; print date: Jul. 24, 2014.

* cited by examiner

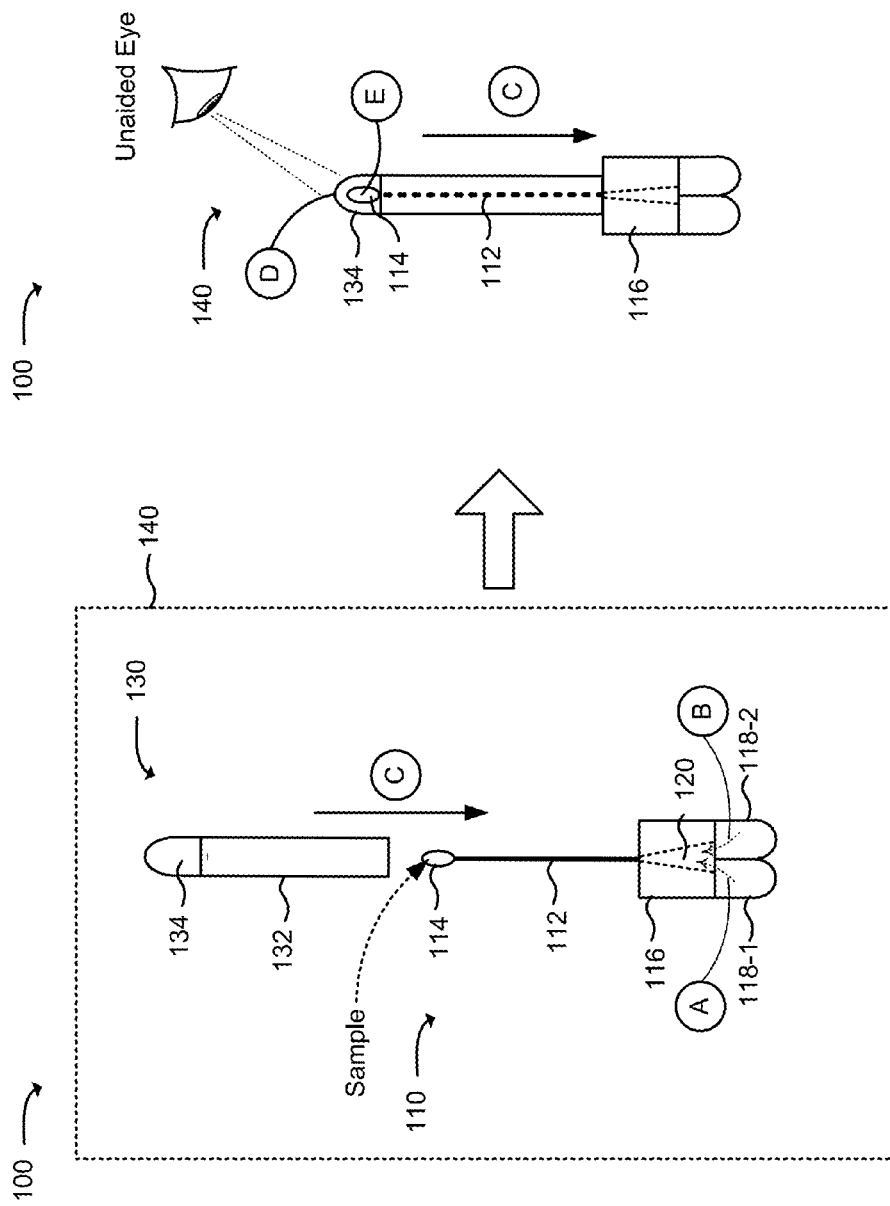

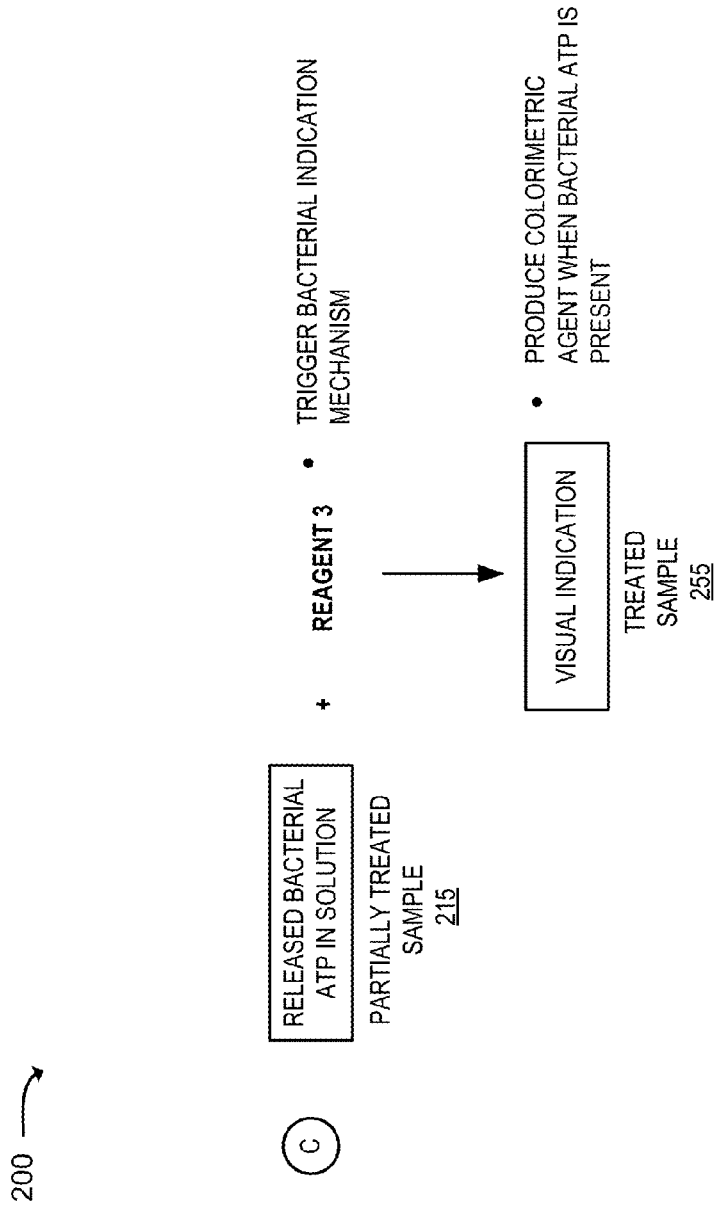

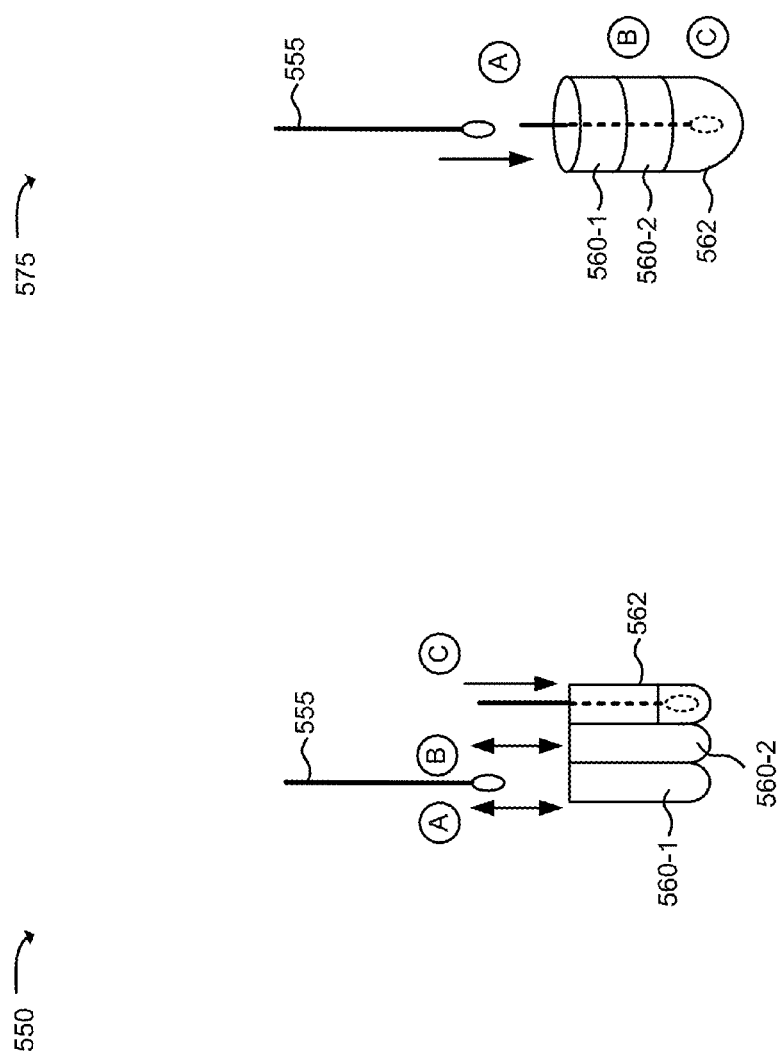

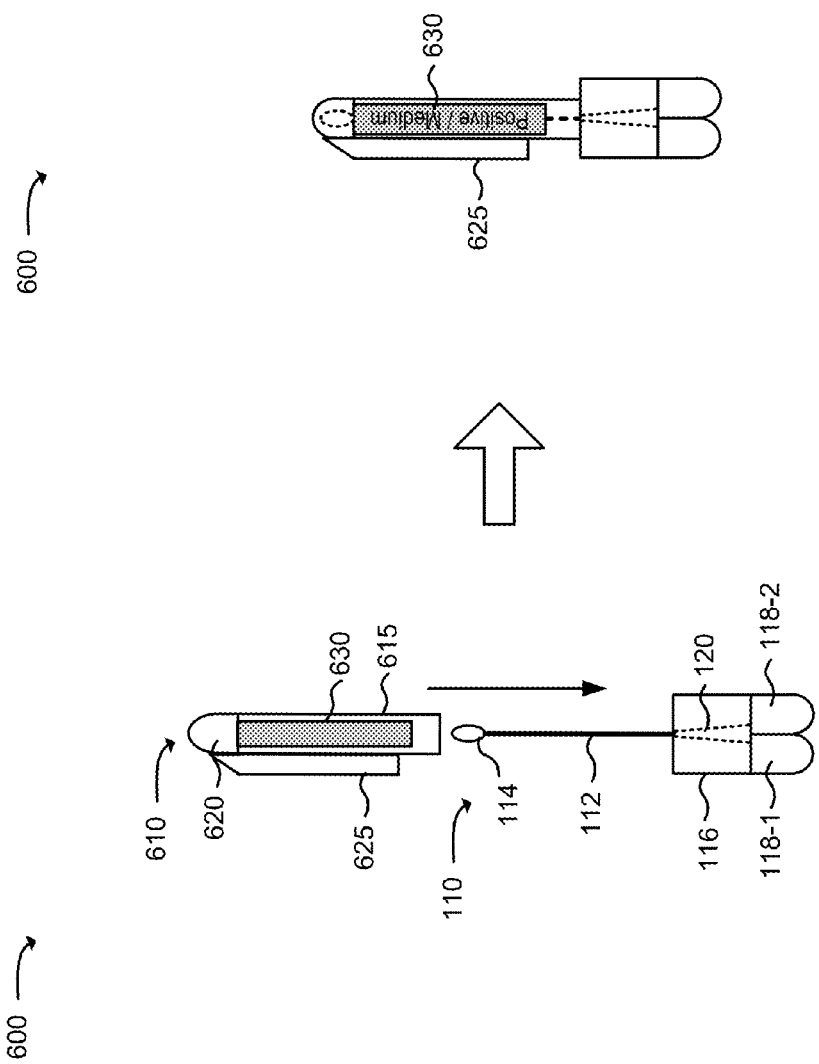

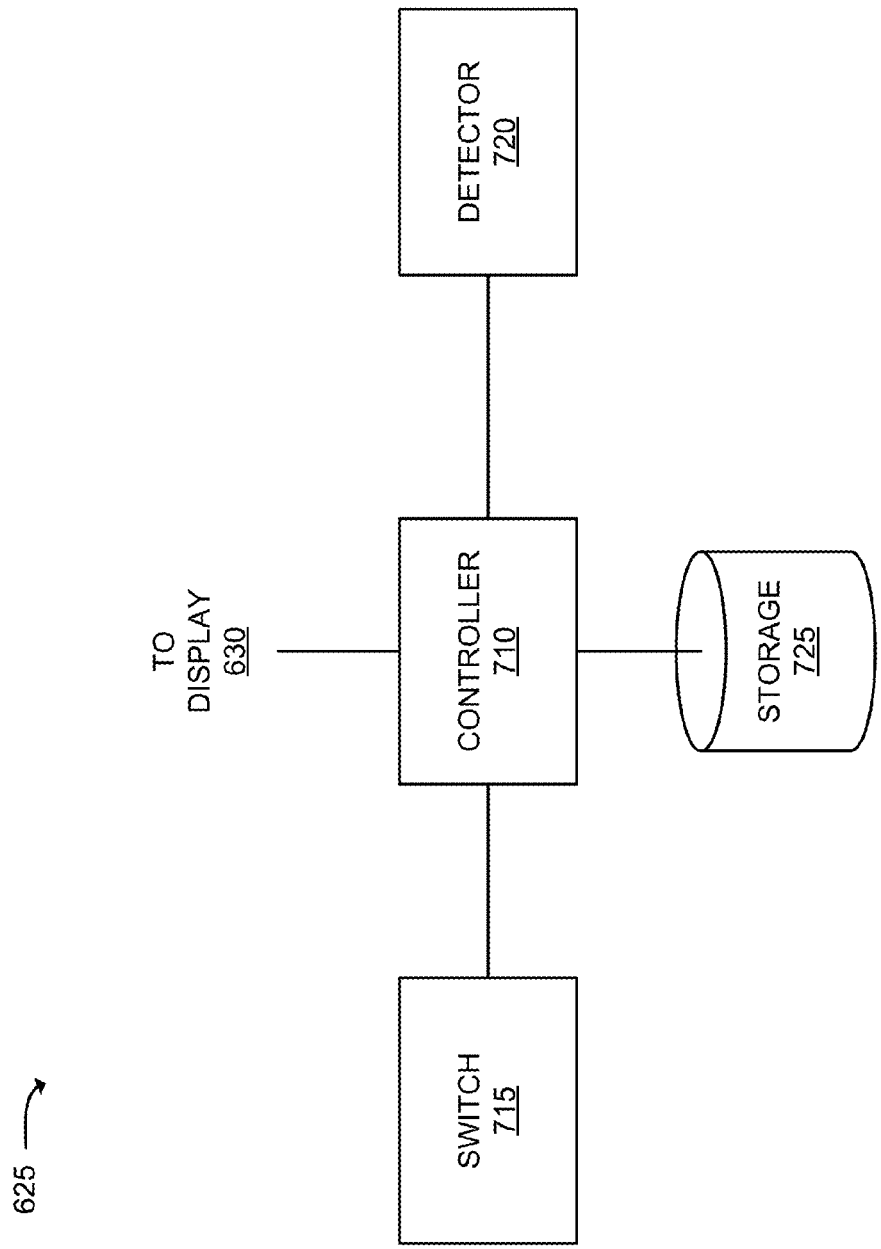

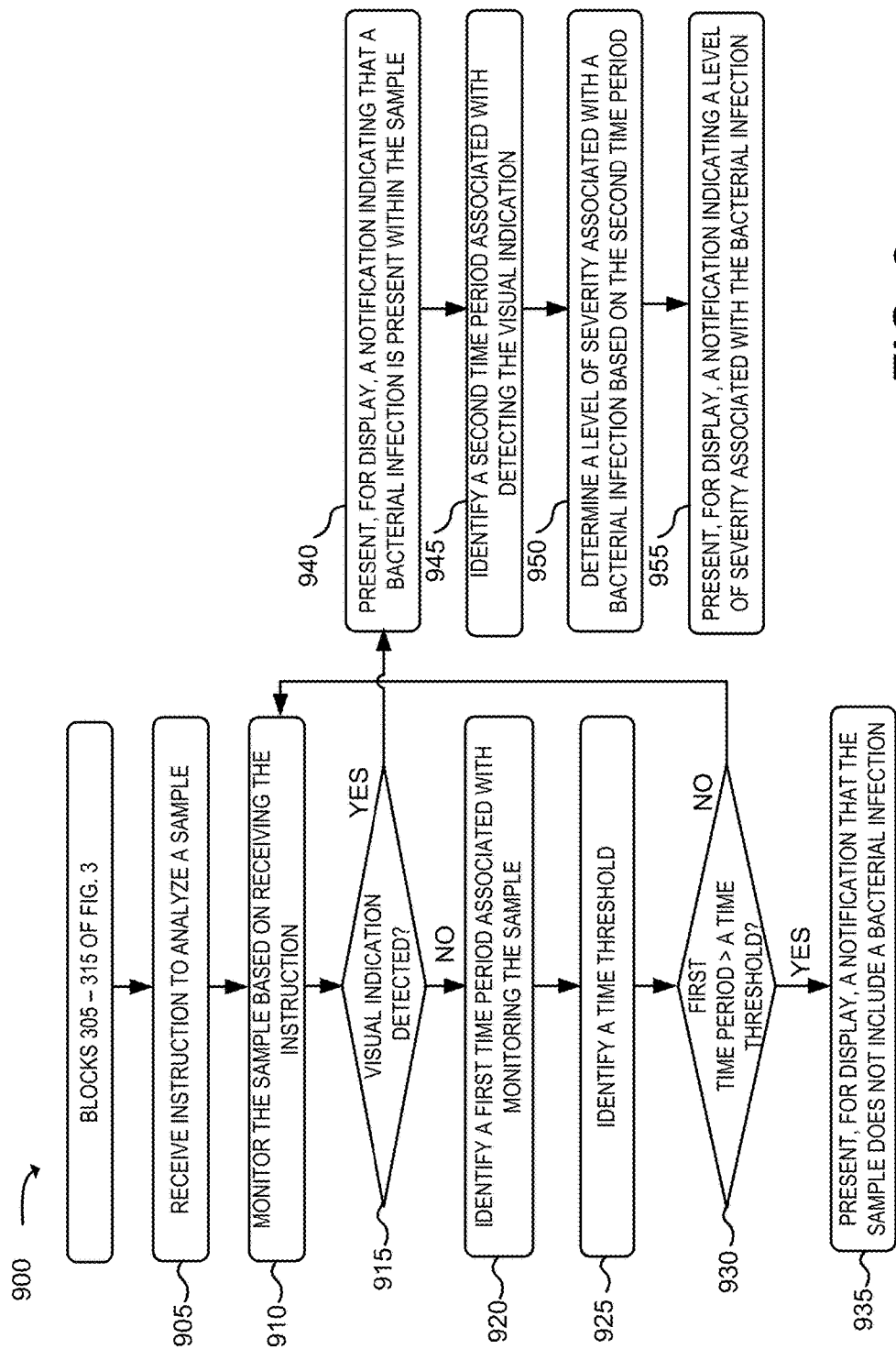

DISTINGUISHING BETWEEN A BACTERIAL AND NON-BACTERIAL INFECTION AT THE POINT OF CARE

REFERENCE TO RELATED APPLICATION

This application a divisional application of U.S. Utility patent application Ser. No. 13/673,615, filed Nov. 9, 2012, the entire contents of the utility patent application being incorporated herein by reference.

BACKGROUND

Doctors often prophylactically prescribe antibiotics for patients that exhibit symptoms that are equally attributable to some types of bacterial infections as well as some types of non-bacterial infections (e.g., viral infections). When the symptoms are caused by a bacterial infection, antibiotics taken by the patient may be an effective remedy to the bacterial infection, which may cause the symptoms to subside. When the symptoms are caused by a non-bacterial infection, antibiotics are not an effective remedy. The problem of over-prescribing of antibiotics is well known with increasing numbers of bacterial strains becoming more and more resistant to antibiotics. It is also well known that prophylactically prescribing antibiotics may contribute to the over-prescribing problem.

The doctor may avoid prophylactically prescribing antibiotics by determining whether the patient suffers from a bacterial infection or a non-bacterial infection based on results of tests performed on a sample taken from the patient at the point of care. While sending samples to a clinical laboratory for testing and waiting for the results (which may take days to obtain) before prescribing antibiotics may help to avoid over-prescribing antibiotics, it is not normally performed in practice due to potential increases in patient healthcare costs (due to multiple visits) and prolonging patient discomfort due to symptoms caused by a bacterial infection.

SUMMARY

According to one implementation, described herein, a method for determining whether a sample, obtained by a patient, includes a bacterial infection may include obtaining, from the patient, the sample that includes a plurality of cells of the patient; applying, to the sample, one or more first reagents to cause adenosine triphosphate (ATP) to be released from bacterial cells, when the plurality of cells include the bacterial cells; and applying, to the sample, a second reagent, in liquid form, to react with the ATP that is released from the bacterial cells, when the plurality of cells include the bacterial cells. The reaction with the ATP may form a colorimetric agent that can be detected by an unaided eye of a medical practitioner. The method may also include determining whether the colorimetric agent is detected; identifying a time period from when the second reagent is applied to when the colorimetric agent is detected; and determining that the patient has the bacterial infection when the time period is less than a threshold. The threshold may correspond to a duration of a point of care office visit between the patient and the medical practitioner.

According to another implementation, described herein, a method for performing an assay on a sample from a patient to detect a bacterial infection or a severity level of the bacterial infection, may include obtaining, from the patient, the sample that includes a plurality of cells of the patient; applying, to the sample, one or more first reagents to cause adenosine triphosphate (ATP) to be released from bacterial cells when the sample includes the bacterial cells; and applying, to the sample, a second reagent in liquid form to cause the second reagent to react with the released ATP when the sample includes the bacterial cells. The reaction may form a colorimetric agent having a concentration that is based on a quantity of the released ATP. The method may also include detecting whether the sample has changed in appearance. The change in appearance being detectable by an unaided eye of a medical practitioner when the concentration of the colorimetric agent is greater than a threshold. The method may further include identifying, when the change in appearance is detected, a time period from when the second reagent is applied to the sample to when the change in appearance is detected; and determining a level of severity, of the bacterial infection, based on the time period. The level of severity may correspond to at least one of: a first level of severity when the time period is less than a duration of a point of care visit by a first amount, or a second level of severity, that is more severe than the first level of severity, when the time period is less than the duration of the point of care visit by a second amount, where the second amount is greater than the first amount.

According to a further implementation, described herein, a method for determining a level of severity of a bacterial infection within a sample, obtained from a patient, may include receiving the sample; applying, to the sample, a first reagent to release and remove background adenosine triphosphate (ATP) from the sample when the sample includes somatic cells of the patient; applying, to the sample, a second reagent to release ATP from bacterial cells of the patient when the sample includes the bacterial cells; and applying, to the sample, a third reagent to react with the released ATP to form a colorimetric agent when the sample includes the bacterial cells. The method may also include monitoring, the sample, to detect whether the colorimetric agent causes the reagent to change in appearance; and detecting that the reagent has changed in appearance. Detecting that the reagent has changed in appearance may be detectable by an unaided eye of an observer or without using a luminometer or optical amplification device. The method may also include identifying a time period from a first time when the third reagent is applied to the sample to a second time when the reagent changing in appearance is detected; and determining a level of severity, of the bacterial infection, based on the time period. The level of severity corresponding to at least one of a first level of severity when the time period is less than a threshold by a first amount, where the threshold is associated with a typical duration of a point of care visit between the patient and a medical practitioner, or a second level of severity when the time period is less than the threshold by an amount that is less than the first amount, where the second level of severity is less severe than the first level of severity.

BRIEF DESCRIPTION OF THE DRAWINGS

FIGS. 1A-1D are diagrams of an overview of an example implementation described herein;

FIGS. 2A and 2B are diagrams of an example reaction that triggers a bacterial indication mechanism, within a sample taken from a patient, that enables a visual indication of whether a bacterial infection exists within the sample;

FIGS. 5A-5C are diagrams of example test devices that may be used to analyze a sample, obtained from a patient, for the presence and/or severity of a bacterial infection;

FIGS. 6A and 6B are diagrams of another example test device that may be used to automatically analyze a sample, obtained from a patient, for the presence and/or severity of a bacterial infection;

FIG. 7 is a diagram of example components of a portion of the test device of FIG. 6;

FIG. 9 is a flow chart of an example process for determining the presence and/or severity of a bacterial infection within a sample taken from a patient;

DETAILED DESCRIPTION OF PREFERRED EMBODIMENTS

Figure 1A:
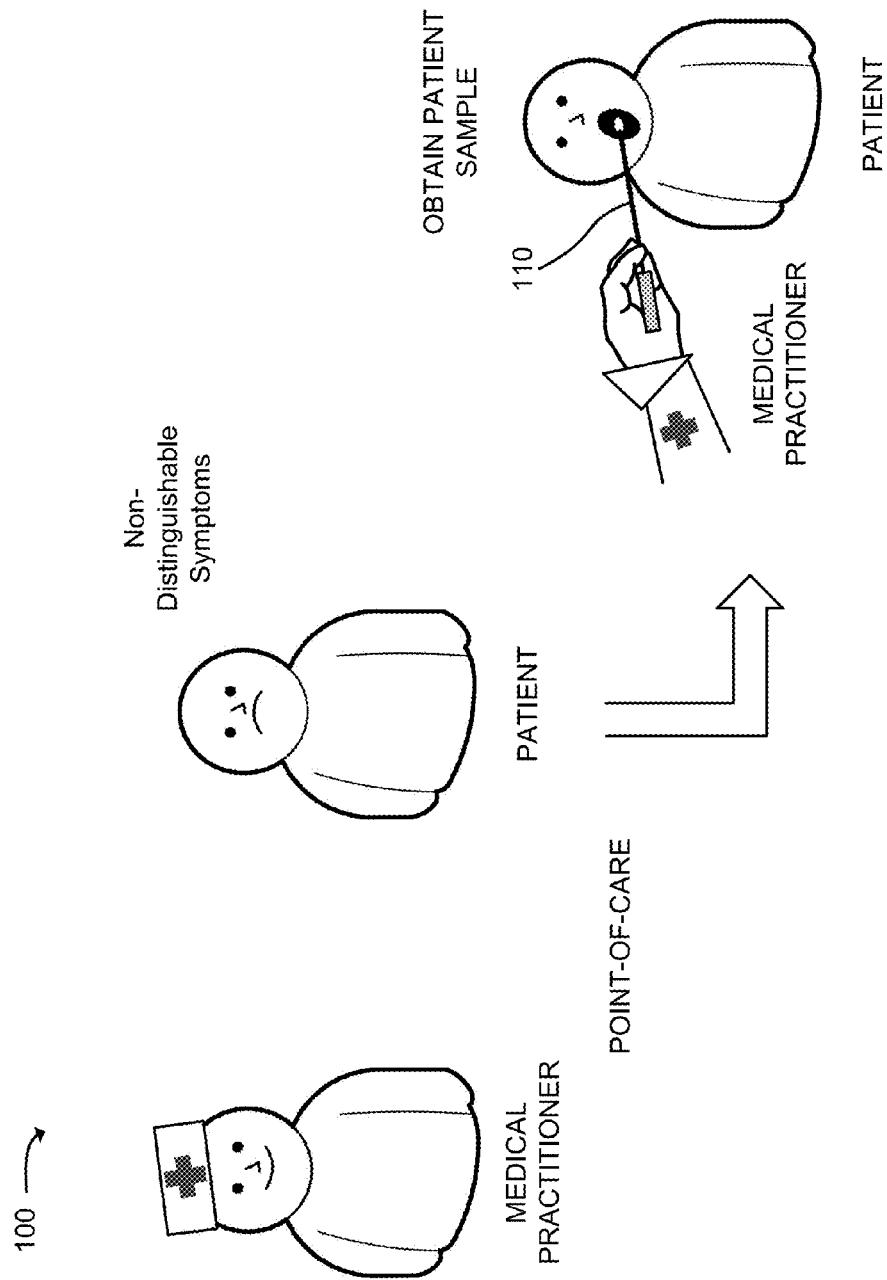

The following detailed description refers to the accompanying drawings. The same reference numbers in different drawings may identify the same or similar elements.

Technologies and/or techniques, described herein, may enable a test device to determine whether a patient is suffering from a bacterial infection or a non-bacterial infection (e.g., a viral infection). The technologies and/or techniques may enable the test device to be used, by an operator (e.g., a medical doctor, a nurse, a physician's assistant, or some other medical practitioner), to obtain a sample from the patient and to analyze the sample for the presence of a bacterial infection. The technologies and/or techniques may enable the test device to apply reagents to the sample, which may cause, within a short period of time (e.g., within 10 seconds, 30 seconds, 1 minute, 5 minutes, 10 minutes, etc.), the one or more of the reagents to change in appearance when the sample includes a bacterial infection. The change in appearance may include a change in color, pattern, texture, etc. (hereinafter referred to a "positive indication"). The one or more reagents may not change in appearance (hereinafter referred to as a "negative indication") when the bacterial infection is not present within the sample.

The technologies and/or techniques may enable the test device to identify a time period associated with detecting a positive indication with respect to a sample and may determine a relative level of severity of the bacterial infection based on the time period. The positive indication or negative indication may be discernable to the unaided eye of the operator without the aid of a sensing or an amplifying device that is distinct from the test device. The term unaided eye may generally correspond to an operator with normal vision (e.g., 20/20 vision) with or without the use of corrective lenses (e.g., eye glasses, contact lenses, etc.). The sensing or amplifying device may include any device other than corrective lenses (e.g., a luminometer, or some other light detecting device), that senses light and/or color changes that are not discernable to the unaided eye and/or that magnifies an object to a level that is greater than that of the unaided eye.

The technologies and/or techniques may enable the operator to determine, within the short period of time and at the point of care (e.g., during the patient's visit to the medical facility, doctor's office, hospital, etc.), whether to prescribe antibiotics as a remedy based on whether the test device generates a positive indication or a negative indication. The technologies and/or techniques may enable the presence a bacterial infection or the level of severity thereof to be determined using a test device at the point of care and without the use of an amplifying or sensing device or mechanism. This may enable the test device to be manufactured inexpensively enough to be disposable and to be widely used at the point of care by a medical practitioner (e.g., a physician, a nurse, etc.) or, in some instances, by the patient at home. The test device may also, or alternatively, aid the practitioner in determining dosage levels or of the antibiotics and/or other remedies based on the level of severity of the bacterial infection. The technologies and/or techniques may preclude laboratory tests (e.g., growing cultures, etc.) from being conducted, which may reduce health care costs and/or decrease the amount of time associated with conducting the laboratory tests. The technologies and/or techniques may also mitigate the problem associated with prophylactically prescribing and/or over-prescribing antibiotics when patients are not suffering from bacterial infections.

FIGS. 1A-1D are diagrams of an overview 100 of an example implementation described herein. As illustrated in FIG. 1A, overview 100 may include an operator (e.g., a medical doctor, a nurse, a physician's assistant, or some other medical practitioner) and a patient in a point-of-care environment (e.g., a medical clinic, a doctor's office, a hospital, etc.). Assume, in the description below, that the operator identifies symptoms, exhibited by the patient, the cause of which are not distinguishable between a bacterial infection or a viral infection (e.g., shown as non-distinguishable symptoms). The operator may use a sample device 110 to obtain a sample from the throat of the patient. The operator may use sample device 110 to process the sample obtained from the patient. While the description below describes the sample as being obtained from the throat of the patient, in other implementations, the sample may be obtained in a different way, such as from a nose, eye, skin lesion, wound, vagina, urethra, spinal fluid sample, stool sample, urine sample, etc. associated with the patient.

As illustrated in FIG. 1B overview 100 may include sample device 110 and a test module 130. Sample device 110 and test module 130 may collectively correspond to a test device 140 (e.g., as shown by the dashed box 140 of FIG. 1B). Sample device 110 may include a collection of components, such as a tube 112, a swab 114, and a handle 116.

Tube 112 may include a hollow cylinder with a first end on which swab 114 is attached and a second end that is attached to handle 116. Swab 114 may include material (e.g., cotton, polyester, etc.) that is suitable for obtaining and/or absorbing a sample from a patient. Handle 116 may be attached to tube 112 and may include a pair of reservoirs 118-1 and 118-2 (hereinafter referred to collectively as "reservoirs 118" and individually as "reservoir 118"), and a channel 120. Reservoir 118 may include a chamber that stores a reagent solution, to be described in greater detail below with respect to FIG. 2A. Additionally, or alternatively, reservoir 118 may be made of a suitable material (e.g., plastic, etc.) that enables reservoir 118 to be mechanically compressed (e.g., squeezed, crushed, collapsed, etc.) by an operator in a manner that causes the reagent solution to be evacuated from reservoir 118 and to enter channel 120. Channel 120 may represent a hollow cavity, cylinder, tube, etc., within handle 116 via which reagent solution is permitted to flow from reservoir 118, via channel 120, and into tube 112. Thus, when reservoir 118 is compressed, the reagent may flow from reservoir 118, to swab 114, via channel 120 and tube 112.

Test module 130 may include a collection of components, such as a cylinder 132, and a test chamber 134. Cylinder 132 may represent a hollow cylinder with a first end that is open to permit the insertion of tube 112 and swab 114 and a second end to which test chamber 134 is attached. Cylinder 132 may also, or alternatively, be made of a material that is sufficiently rigid to maintain shape, to permit repeated insertion or removal of tube 112 and swab 114, and/or to be repeatedly fastened to, or unfastened from, sample device 110. Test chamber 134 may include a chamber that stores one or more second reagent solutions, to be described in greater detail below with respect to FIG. 2B. Additionally, or alternatively, test chamber 134 may be made of a suitable material that enables swab 114 (e.g., that includes the sample and the first reagents from sample device 110) to perforate and enter test chamber 134 when a length of tube 112 and swab 114 are inserted into test module 130. The suitable material, in this example, may be sufficiently transparent such that any change in appearance of the second reagent solutions within test chamber 134 can be viewed by the operator with an unaided eye (e.g., without the aid of a sensing or an amplifying device, such as an optical amplifier, a magnification device, etc.).

By way of example, the operator may compress one or both reservoirs 118 to cause one or more first reagents to travel, via channel 120 and tube 112, to saturate the sample that exists on or within swab 114 (e.g., as shown by the dashed arrows identified by indications A and B). The first reagents may cause background adenosine triphosphate (ATP) to be released from non-bacterial cells (e.g., somatic cells) within the sample and to be removed from solution or otherwise rendered inert. Additionally, or alternatively, the first reagents may cause ATP from any bacterial cells within the sample to be released into solution within swab 114. Thus, when a quantity of bacterial cells, within the sample, is less than a threshold, no ATP, or a negligible quantity thereof, will be released into solution.

Additionally, or alternatively, the operator may place test module 130 over tube 112 and swab 114 (e.g., as shown by the downward pointing arrow associated with indication C of FIG. 1B). As shown in FIG. 1C, the operator may insert tube 112 and swab 114 into test module 130 until swab 114 perforates test chamber 134 (e.g., as shown by indication D in FIG. 1C). Perforating test chamber 134 may cause swab 114 to be immersed in a solution that includes one or more second reagents, which may enable a bacterial indication mechanism, to be described in greater detail below with respect to FIG. 2B, to be triggered. The second reagents may react with the ATP to trigger the bacterial indication mechanism that creates a colorimetric indication (e.g., on swab 114 or within the second reagent solution) that is discernable, within a short period of time (e.g., 10 seconds, 30 seconds, 1 minute, 2 minutes, 5 minutes, 10 minutes, etc.), to the unaided eye of the operator (e.g., as shown by indication E of FIG. 1C).

The quantity of devices and/or components, associated with test device 140, is identified in FIGS. 1B and 1C for explanatory purposes only. In practice, test device 140 may include additional devices and/or components; fewer devices and/or components; different devices and/or components; or differently arranged devices and/or components than illustrated in FIGS. 1B and 1C. Alternatively, or additionally, one or more of the devices and/or components of test device 140 may perform one or more functions described as being performed by another one or more of the devices and/or components of test device 140. Additionally, or alternatively, while FIGS. 1B-1C describe reservoirs 118 and test chamber 134 as being compressible, in some implementations, reservoir 118 and/or test chamber 134 may be implemented in a number of different ways, such as, for example, a syringe mechanism and/or some other known mechanism.

Figure 1D:
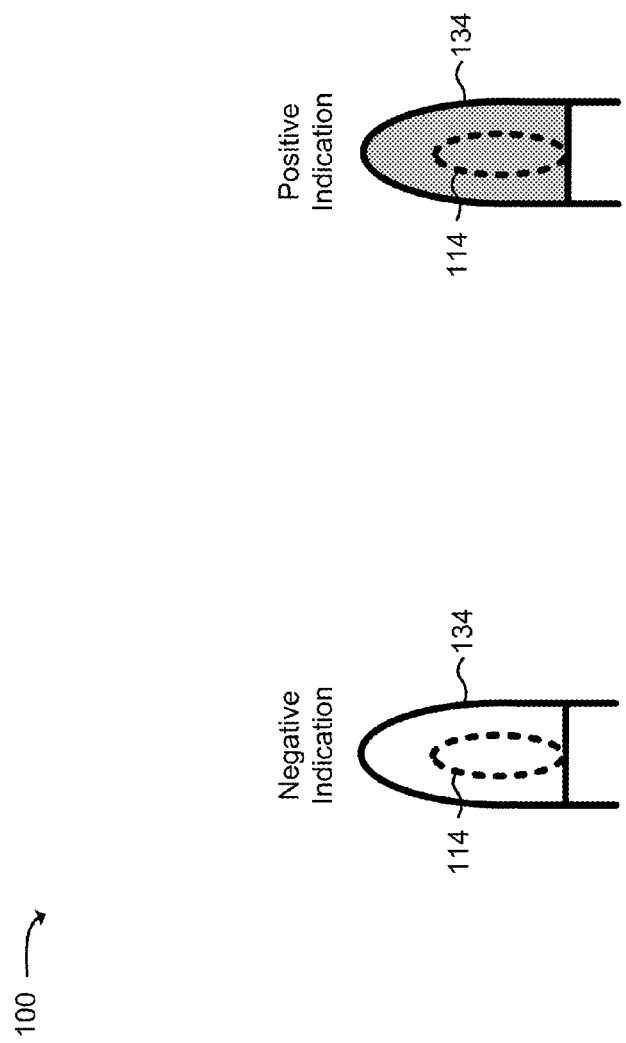

As shown in FIG. 1D, overview 100 may include test chamber 134 with which a negative indication and a positive indication are associated. The negative indication (e.g., shown as unshaded test chamber 134) may occur when the colorimetric indication is not created by the second reagent solution due to the absence of a bacterial infection within the sample (e.g., when the sample does not include ATP). The operator may, based on the negative indication, refrain from prescribing antibiotics for the patient based on the indication that the symptoms exhibited by the patient are not caused by a bacterial infection. The positive indication (e.g., shown as shaded test chamber 134) may occur when the colorimetric indication is created by the second reagent solution due to the presence of a bacterial infection within the sample (e.g., when the sample includes ATP). In this example, the positive indication may occur when the second reagent changes from a first color, pattern, and/or texture (e.g., associated with the unshaded test chamber 134 on the left side of FIG. 1D) to a second color, pattern, and/or texture, respectively (e.g., associated with the shaded test chamber 134 on the right side of FIG. 1D) that is different than the first color, pattern, or texture. The operator may, based on the positive indication, prescribe antibiotics for the patient based on the positive indication that the symptoms exhibited by the patient are caused by a bacterial infection.

Figure 2A:
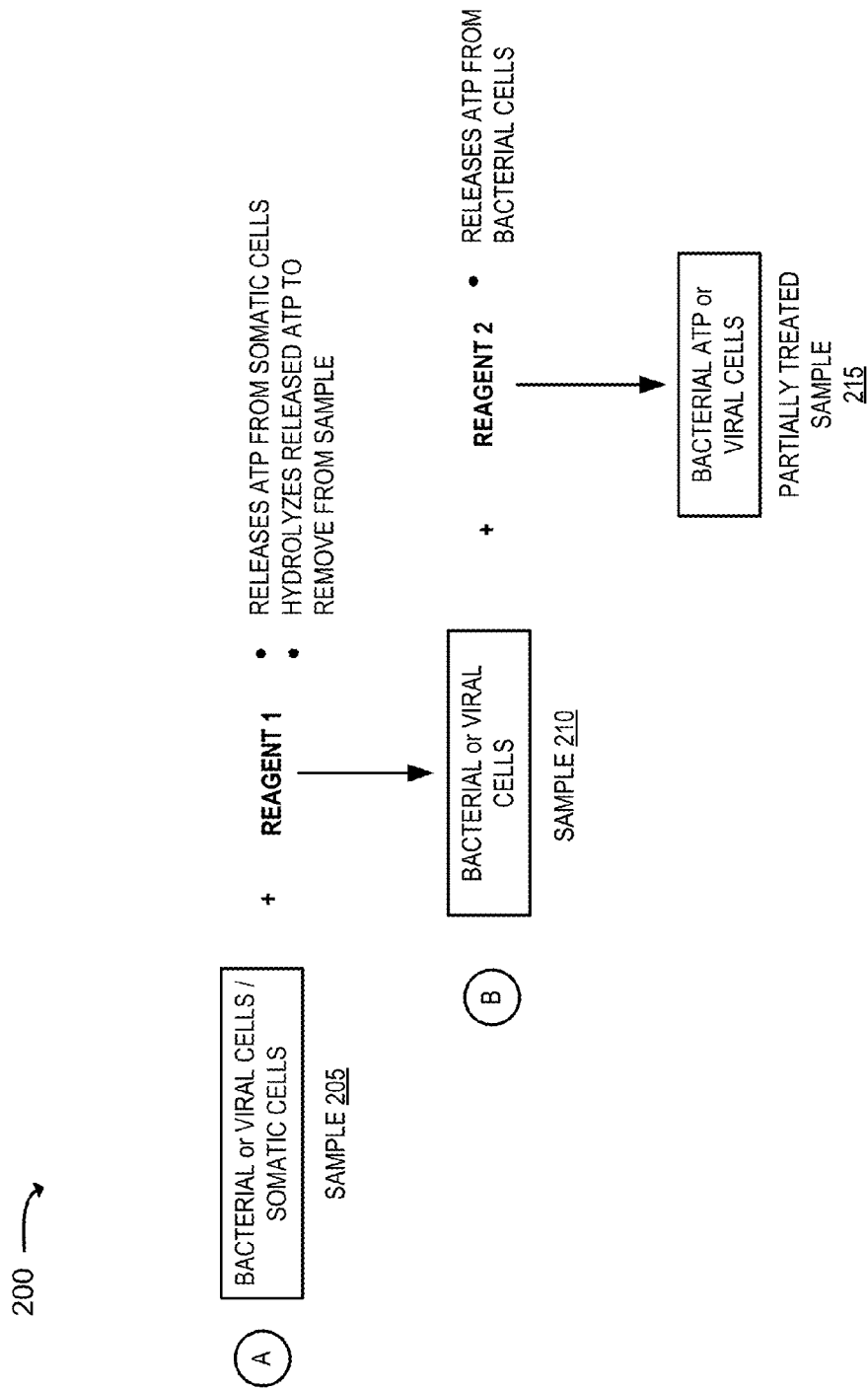

FIGS. 2A and 2B are diagrams of an example reaction 200 that triggers a bacterial indication mechanism, within a sample taken from a patient, to create visual indication of whether a bacterial infection exists within the sample. As illustrated in FIG. 2A, reaction 200 may include applying a first reagent (e.g., reagent 1) to a sample (e.g., sample 205) obtained from a patient (e.g., shown as indication A). The sample may include somatic cells, bacterial cells, viral cells, or some combination thereof. Applying the first reagent to the sample may remove background ATP from somatic cells within the sample. Removing the background ATP from the sample may enable the source of any quantity of ATP within the sample, to be isolated to bacterial cells within the sample. In one example, the first reagent may include a constituent agent (e.g., benzalkonium chloride or some other somatic cell ATP releasing agent) that in known to cause somatic cell membranes to become permeable to background ATP, which enables the background ATP to be released from the somatic cells. The first reagent may also, or alternatively, include a different constituent agent that is known to hydrolyze and/or bind the released background ATP (e.g., Somase and/or some other hydrolyzing or binding agent), which renders the released background ATP inert, inactive, and/or effectively removed from the sample to create a processed sample (e.g., sample 210). Removing the released background ATP from the sample may create the processed sample that includes bacterial cells and/or viral cells.

Reaction 200 may also, or alternatively, include applying another first reagent (e.g., reagent 2) to the processed sample (e.g., shown as indication B). Applying the other first reagent to the processed sample may cause ATP to be released from any bacterial cells that exist within the processed sample. In one example, the other first reagent may include a particular constituent agent that is known to cause bacterial cell membranes to become permeable to ATP (e.g., a nucleotide releasing buffer (NRB) or some other nucleotide releasing agent), which enables the ATP to be released from the bacterial cells to create a partially treated sample (e.g., partially treated sample 215). The partially treated sample may include the ATP released from the bacterial cells.

As illustrated in FIG. 2B, reaction 200 may include applying a second reagent (e.g., reagent 3) to the partially treated sample (e.g., partially treated sample 215) (e.g., shown as indication C). Applying the second reagent to the partially treated sample may trigger a bacterial indication mechanism within the partially treated sample to create a treated sample (e.g., treated sample 255). The bacterial indication mechanism may generate a visual indication (e.g., a positive indication or negative indication that is discernable to the unaided eye) of whether bacterial cells exist within the treated sample. For example, the bacterial indication mechanism may be triggered when a first constituent agent, such as an enzyme that catalyzes glucose (e.g., hexokinase at approximately 125 enzyme units (U)/milligram (mg), and 0.5%-2.0% of the second reagent by volume; and/or some other glucose catalyzing enzyme), a second constituent agent (e.g., glucose at approximately 2%-10% of the second reagent by volume), and a third constituent reagent (e.g., magnesium sulfate heptahydrate at a concentration of approximately 2 moles/liter (M) and 2.0%-6.0% of the second reagent by volume) within the second reagent, react with the released bacterial ATP within the treated sample to produce adenosine diphosphate (ADP).

The ADP and a fourth constituent agent of the second reagent, such as a cytosolic enzyme (e.g., glucose 6 phosphate dehydrogenase at approximately 450 U/mg, and 0.1%-0.6% of the second reagent by volume; and/or some other cytosolic enzyme), react with a fifth constituent agent of the second reagent, such as a dinucleotide (e.g., Nicotinamide Adenine Dinucleotide (NAD) at approximately 5.0%-10.0% of the second reagent by volume; and/or some other dinucleotide), which reduces the fifth constituent agent (e.g., NAD) to NADH (e.g., by the addition of a hydrogen ion).

The NADH may react with a sixth constituent agent (e.g., diaphorase at approximately 110 U/mg, and 0.5%-3.0% of the second reagent by volume) and a seventh constituent agent (e.g., formazane dye at approximately 6.0-15% of the second reagent by volume) of the second reagent, which reduces the formazane dye (e.g., by the addition of a hydrogen ion) to produce a colorimetric agent (e.g., resulting in a change of appearance of the second reagent). Additionally, or alternatively, the reduction of the formazane dye may cause the NADH to be converted back to the fifth constituent reagent (e.g., NAD), thus, recycling the fifth constituent agent to be used again and again in the reaction with the ADP and the fourth constituent agent (e.g., glucose 6 phosphate dehydrogenase). The second reagent may also, or alternatively, include a buffer solution, such as, for example, magnesium sulfate and ethylenediaminetetraacetic acid (EDTA) (e.g., at approximately 2.0 M and 30.0%-50.0% of the second reagent by volume) and/or some other buffer solution.

The recycling of the fifth constituent agent may, thus, act as an amplification mechanism by producing more and more colorimetric agents (e.g., the reduced formazane dye) so long as all of the constituent agents of the second reagent are present in excess. Furthermore, the amplification mechanism may enable sufficient amounts of the reduced formazane dye to be produced so as to generate a visual indicator that can be detected by an operator (e.g., a medical doctor, a nurse, a physician's assistant, or some other medical practitioner) with an unaided eye (e.g., without the aid of a sensing or an amplification device).

Thus, the second reagent may include sufficient quantities of the constituent agents such that samples including relatively large quantities of ATP (e.g., released from a large amount of bacterial cells within a sample taken from a patient with a severe bacterial infection), do not exhaust any of the constituent agents, which may otherwise cause the reaction to reduce the formazane dye to be inhibited or stopped. Having sufficient quantities of the constituent agents may, thus, enable the colorimetric indicator to be detected earlier when severe bacterial infections are present in the sample than when minor bacterial infections are present within the sample (e.g., associated with fewer bacterial cells and thus a smaller quantity of ATP).

While the description above with respect to reaction identifies the second reagent as including a number of particular constituent agents, in some other implementations, there may be additional constituent agents, fewer constituent agents, or different constituent agents than those described above with respect to the second reagent. For example, the first constituent agent may include phosphofructokinase and/or glucose dehydrogenase; the second constituent agent may include lactose; the third constituent agent may include magnesium hexahydrate; the fourth constituent agent may include lactate dehydrogenase; the fifth constituent agent may include flavin adenine dinucleotide; the sixth constituent agent may include glutathione reductase and/or lipoyl dehydrogenase; and/or the seventh constituent agent may include resazurin and/or some other dye.

Figure 3:
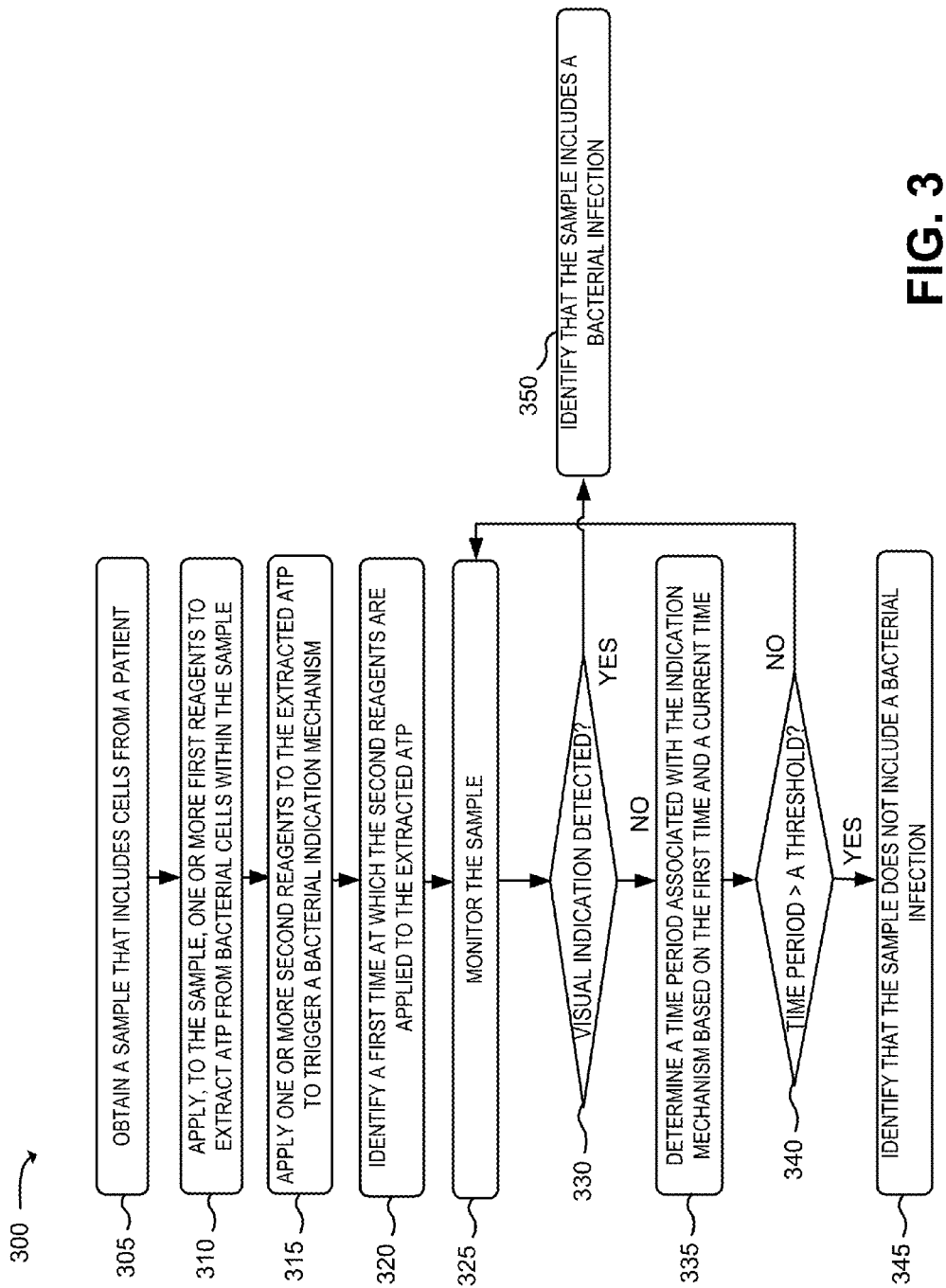
FIG. 3 is a flow chart of an example process for determining whether a sample, taken from a patient, includes a bacterial infection.

FIG. 3 is a flow chart of an example process 300 for determining whether a sample, taken from a patient, includes a bacterial infection. In an example implementation, process 300 may be performed by test device 140. Additionally, or alternatively, some or all of process 300 may be performed by a device or collection of devices separate from, or in combination with, test device 140.

As shown in FIG. 3, process 300 may include obtaining a sample that includes cells from a patient (block 305). For example, an operator (e.g., a medical doctor, a nurse, a physician's assistant, or some other medical practitioner) may examine a patient and determine that the patient is exhibiting symptoms caused by a bacterial or non-bacterial infection (e.g., a viral infection). The practitioner may obtain a sample from the patient that includes the patient's cells. The sample may be obtained in a number of ways, such as from the patient's mouth and/or throat; from a skin lesion and/or wound on the patient; from the patient's spinal fluid, etc. In an example implementation, the practitioner may use test device 140 (e.g., sample device 110) to obtain the sample in a manner similar to that described above with respect to FIG. 1B. The sample may include bacterial cells when the patient is suffering from a bacterial infection, non-bacterial cells when the patient is suffering from a non-bacterial infection, and/or somatic cells.

As also shown in FIG. 3, process 300 may include applying, to the sample, one or more first reagents to extract ATP from bacterial cells within the sample (block 310). For example, the operator may apply a first reagent (e.g., reagent 1 of FIG. 2A) to the sample. The application of the first reagent may cause the somatic cells to become permeable, which enables background ATP to be released from the somatic cells within the sample. The first reagent may, for example, include a first constituent agent (e.g., benzalkonium chloride and/or some other somatic cell extractant) that causes the membranes of the somatic cells to become permeable to background ATP. The first reagent may also, or alternatively, include a second constituent agent (e.g., Somase (ATPase), and/or some other hydrolyzing and/or binding agent) that hydrolyzes and/or binds the released background ATP thereby rendering the released background ATP inert, inactive, and/or effectively removed from the sample.

Additionally, or alternatively, the operator may use test device 140 (e.g., sample device 110), to apply the first reagent to the sample. In this example, the operator may compress (e.g., by squeezing, pinching, etc.) a first reservoir (e.g., reservoir 118-1) of test device 140 that causes the first reagent to flow to, be dispensed into, and/or be applied to the sample via channel 120, tube 112, and swab 114 in a manner similar to that described above with respect to FIG. 1B.

Additionally, or alternatively, the operator may apply another first reagent (e.g., reagent 2 of FIG. 2A) to the sample. The application of the other first reagent may cause the bacterial cells (e.g., if they exist within the sample) to become permeable to ATP, which enables ATP to be released from the bacterial cells. In an example implementation, the other first reagent may include a nucleotide releasing agent (e.g., nucleotide releasing buffer (NRB) and/or some other nucleotide releasing agent). Additionally, or alternatively, the operator may use test device 140 (e.g., sample device 110), to apply the other first reagent to the sample. In this example, the operator may compress a second reservoir (e.g., reservoir 118-2) of test device 140 that causes the other first reagent to flow to and be dispensed into and/or applied to the sample via channel 120, tube 112, and swab 114 in a manner similar to that described above with respect to FIG. 1B.

As further shown in FIG. 3, process 300 may include applying, to the sample, one or more second reagents to the extracted ATP to trigger a bacterial indication mechanism (block 315); identifying a first time at which the second reagents are applied (block 320); and monitoring the sample (block 325). For example, the operator may apply a second reagent (e.g., reagent 3 of FIG. 2B) to the sample. The second reagent may include a number of constituent agents that react with the ATP released from the bacterial cells when the sample includes bacterial cells. The application of the second reagent may, in a manner similar to that described above with respect to FIG. 2B, cause a bacterial indication mechanism to be triggered when the sample includes bacterial cells. The bacterial indication mechanism may create a colorimetric agent that acts as a colorimetric indicator that generates a positive indication (e.g., when the second reagent changes in appearance), visible to the unaided eye and/or without the aid of a sensing or amplifying device, when the sample includes bacterial cells. When the sample does not include bacterial cells, the bacterial indication mechanism may not be triggered, which may not produce the colorimetric indicator (e.g., resulting in a negative indication when the second reagent does not change in appearance).

In an example implementation, the operator may use test device 140 (test module 130) to apply the second reagent to the sample. For example, the operator may, in a manner similar to that described in FIGS. 1B and 1C, insert sample device 110 into test module 130 that causes the sample (e.g., associated with swab 114) to perforate and/or enter a test chamber (e.g., test chamber 134) associated with test module 130. The test chamber may store the second reagent and the sample may be immersed in the second reagent when the sample enters the test chamber.

A first time at which the sample is inserted into the test chamber may be identified (e.g., by an operator of test device 140). The first time may represent a time when the bacterial indication mechanism is initiated. The operator may monitor the sample by viewing the sample via the transparent material of the test chamber to determine whether the second reagent, within the test chamber, changes in appearance (e.g., changes in color, pattern, texture, etc.).

As still further shown in FIG. 3, if a visual indication is not detected (block 330—NO), process 300 may include determining a time period associated with indication mechanism based on the first time and a current time (block 335). For example, the operator may, based on monitoring the sample, determine that the test chamber has not changed in appearance (e.g., has not changed in color, pattern, texture, etc.). In one example, the operator may monitor the sample within test device 140 and may determine that the test chamber (e.g., the second reagent within the test chamber) has not changed in appearance. The operator may identify a second time (e.g., a current time) and may determine a time period, that has occurred since the second reagent was applied to the sample, based on a difference between the first time and the second time.

As also shown in FIG. 3, if the time period is greater than a threshold (block 340—YES), process 300 may include identifying that the sample does not include a bacterial infection (block 345). For example, the operator may compare the time period to a predetermined amount of time (hereinafter referred to as a time threshold) that is associated with the bacterial indication mechanism. When the time period is greater than the time threshold, the operator may determine that the sample does not include cells associated with a bacterial infection. In one example, the operator may determine that test device 140 has generated a negative indication. The operator may use the negative indication to support a diagnosis that the symptoms, exhibited by the patient, are not caused by a bacterial infection.

As further shown in FIG. 3, if the time period is not greater than the threshold (block 340—NO), process 300 may include monitoring the sample (block 325). For example, the operator may determine that the time period is not greater than the time threshold and may continue to monitor the sample to determine whether a positive indication is detected.

As still further shown in FIG. 3, if the visual indication is detected (block 330—YES), process 300 may include identifying that the sample includes a bacterial infection (block 350). For example, the operator may, based on monitoring the sample, observe (e.g., with an unaided eye and/or without the use of a separate sensing or amplifying device) that the test chamber has changed in appearance (e.g., has changed in color, pattern, texture, etc.). For example, the operator may determine that the second reagent has changed from a first color (e.g., a white color or some other first color) to a second color (e.g., a black color or some other second color). The second color may be different than the first color. In one example, the operator may monitor the test chamber of test device 140 and may determine that the third reservoir (e.g., the second reagent within the third reservoir) has changed in appearance, thus, generating a positive indication.

For example, the operator may, based on the positive indication, determine that the sample includes cells associated with a bacterial infection. The operator may use the positive indication to support a diagnosis that the symptoms, exhibited by the patient, could be caused by a bacterial infection.

Additionally, or alternatively, the operator may identify a third time at which the positive indication was detected. The operator may determine a particular time period, associated with the bacterial indication mechanism, based on the first time when bacterial indication mechanism was initiated and the second time when the positive indication was detected. The particular time period, associated with the bacterial indication mechanism, may, in a matter to be described in greater detail below with respect to FIG. 4, be used to identify a level of severity associated with the bacterial infection.

Figure 4:
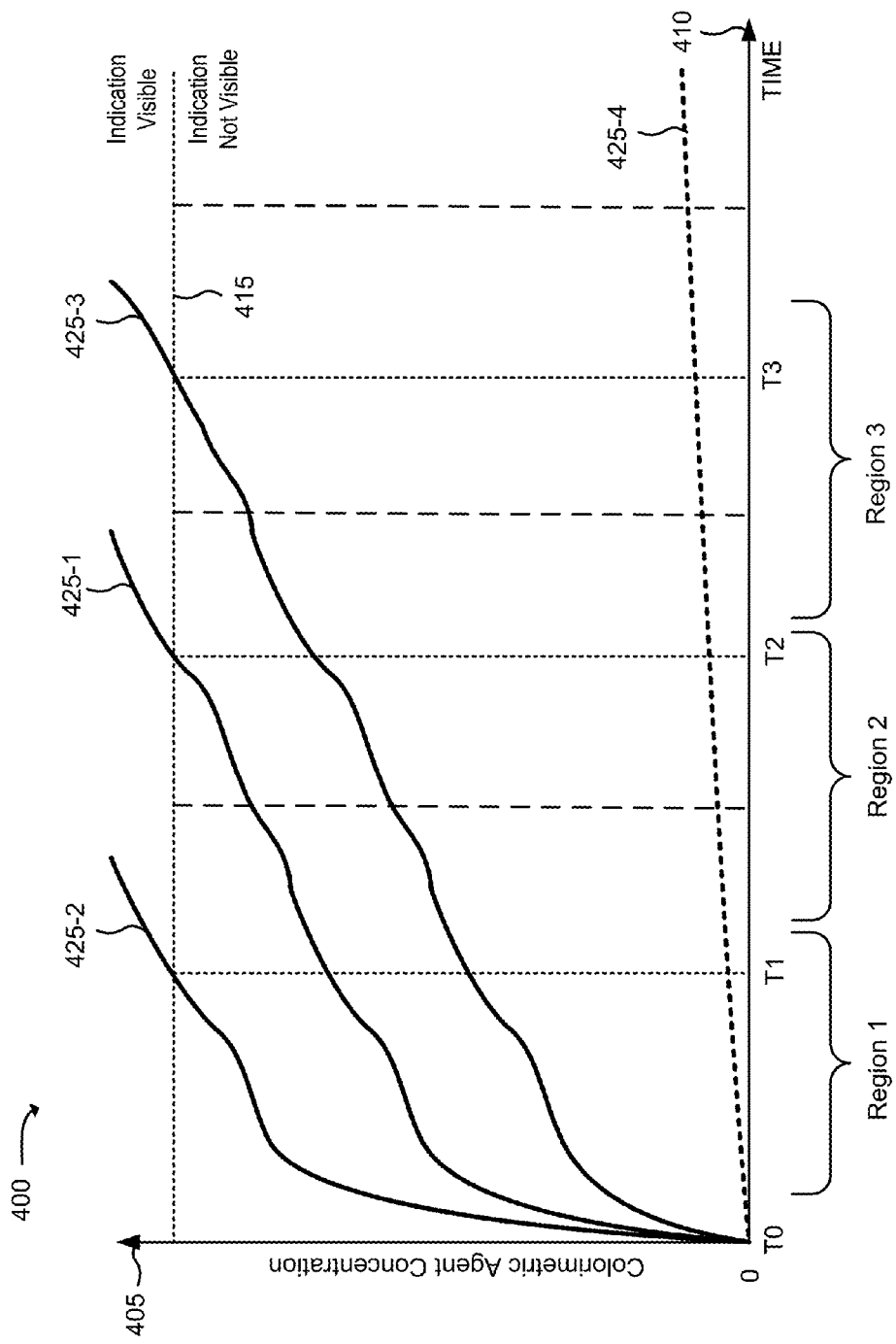
FIG. 4 is a graph that depicts an amount of colorimetric agent that may be generated by a bacterial indication mechanism as a function of time and/or bacterial cell population.

FIG. 4 is a graph 400 that depicts a concentration of colorimetric agent generated by a bacterial indication mechanism as a function of time and/or bacterial cell population. In an example implementation, the colorimetric agent may correspond to reduced formazane dye and/or some other dye as described above with respect to FIG. 2B. As illustrated in FIG. 4, graph 400 may depict a range of concentrations of colorimetric agent within a sample (e.g., shown as vertical axis 405 labeled "colorimetric agent concentration") and a time scale (e.g., shown as horizontal axis 410 labeled "time"). Graph 400 may also identify an indication threshold 415 which specifies a concentration of the colorimetric agent, within the sample, at or above which a positive indication becomes visible to the unaided eye and below which the positive indication does not become visible to the unaided eye (e.g., resulting in a negative indication). Graph 400 may include a group of concentration trends 425-1, . . . , 425-4 (hereinafter referred to collectively as "trends 425" and individually as "trend 425"). Each trend 425 may represent a different concentration of the colorimetric agent (e.g., based on vertical axis 405) that is produced within a sample, as a function of time (e.g., based on horizontal axis 410), by a bacterial indication. The different trends 425 may correspond to different quantities of bacterial cells (hereinafter referred to as "bacterial population") that exist within the sample. Thus, a higher bacterial population may correspond to higher level of severity of infection and a lower bacterial population may correspond to a lower level of severity of infection.

By way of example, assume that a biological indication mechanism has been triggered in a sample in a manner similar to that described above with respect to block 305-325 of FIG. 3. As the second reagent(s) (e.g., reagent 3 of FIG. 2B) reacts with the bacterial cells, within the sample, the colorimetric agent is generated by the reactions associated with the bacterial indication mechanism. As shown by a first trend 425 (e.g., trend 425-1), the amount of the agent, within a first sample (e.g., taken from a first patient), may increase from a first (initial) concentration equal to or approximately zero when the mechanism is triggered at a first time (e.g., shown as T0) to a higher concentration of colorimetric agent as the bacterial mechanism continues over time. Thus, as the reaction continues, the amount of colorimetric agent increases until a second concentration reached that is equal to or greater than indication threshold 415 at a second time (e.g., shown as T2, where T2>T0). When the concentration of the colorimetric agent is equal to or greater than indication threshold 415, the second reagent may change in appearance (e.g., change color, change texture, change pattern, etc.) in a manner that is visible to the unaided eye (e.g., a positive indication) and/or in a manner that does not require the aid of a sensing or an amplifying device. Thus, the positive indication of the first sample may be detected within a first time period (e.g., TP1, where TP1=T2−T0).

Additionally, or alternatively, when the bacterial population, associated with a second sample (e.g., taken from a second patient), is higher than the bacterial population of the first sample, the concentration of the colorimetric agent may increase at a faster rate (e.g., shown as trend 425-2), which may cause the positive indication to be detected at a third time (e.g., T1) that is less than the second time (e.g., where T0<T1<T2) and/or within a second time period (e.g., TP2, where TP2=T1−T0). In this example, the second time period may be less than the first time period (e.g., TP2<TP1). Additionally, or alternatively, while a single trend 425-2 is identified within graph 400 that corresponds to the detection of the positive indication within the second time period that is less than the first time period, there may be one, some, or a continuum of trends 425-2 that correspond to different bacterial populations, within the second sample, that are higher than those associated with the first sample. The continuum of trends 425-2, associated with the second time period may correspond to a first time frame (e.g., region 1) that corresponds to higher bacterial populations than those identified in a second time frame (e.g., shown as region 2).

Additionally, or alternatively, when the bacterial population, associated with a third sample (e.g., taken from a third patient), is less than the bacterial population of the first sample, the concentration of the colorimetric agent may increase at a slower rate (e.g., shown as trend 425-3), which may cause the positive indication to be detected within the third sample at a fourth time (e.g., T3) that is greater than the second time (e.g., where T2<T3) and/or within a third time period (e.g., TP3, where TP3=T3−T0). In this example, the third time period may be greater than the first time period (e.g., TP1<TP3). Additionally, or alternatively, while a single trend 425-3 is identified within graph 400 that corresponds to the detection of the positive indication within the third time period that is greater than the first time period, there may be one, some, or a continuum of trends 425-3 that correspond to different bacterial populations, within the third sample, that are lower than those associated with the first sample. The continuum of trends 425-3, associated with the third time period may correspond to a third time frame (e.g., region 3) that corresponds to lower bacterial populations than those identified in the second time frame (e.g., shown as region 2).

Based on the foregoing, the time at which the positive indication is detected may correspond to a bacterial population associated with a sample, which is related to the level of severity of bacterial infection being suffered by a patient. Thus, a positive indication, in connection with a particular sample, that is detected before a positive indication in connection with a different sample, may indicate a higher level of severity of infection for a particular patient from which the particular sample was taken than a level of severity of infection in a different patent from which the different sample was taken. Similarly, a positive indication, in connection with the particular sample, that is detected after a positive indication in connection with the different sample, may indicate a lower level of severity of infection for the particular patient than the level of severity of infection in the different patient.

A positive indication, in connection with the particular sample, that is detected within approximately the same time period as a positive indication in connection with the different sample, may indicate that the particular patient and the different patient are suffering from respective bacterial infections of an approximately equal level of severity.

When a sample does not include a bacterial infection, such as when the bacterial population within the sample is approximately equal to zero, the bacterial indication mechanism may not be triggered when the second reagent is applied to the sample and/or the concentration of colorimetric agent may not increase to a level that is equal to or greater than indication threshold 415 (e.g., as shown by the dashed trend 425-4).

Figure 5A:
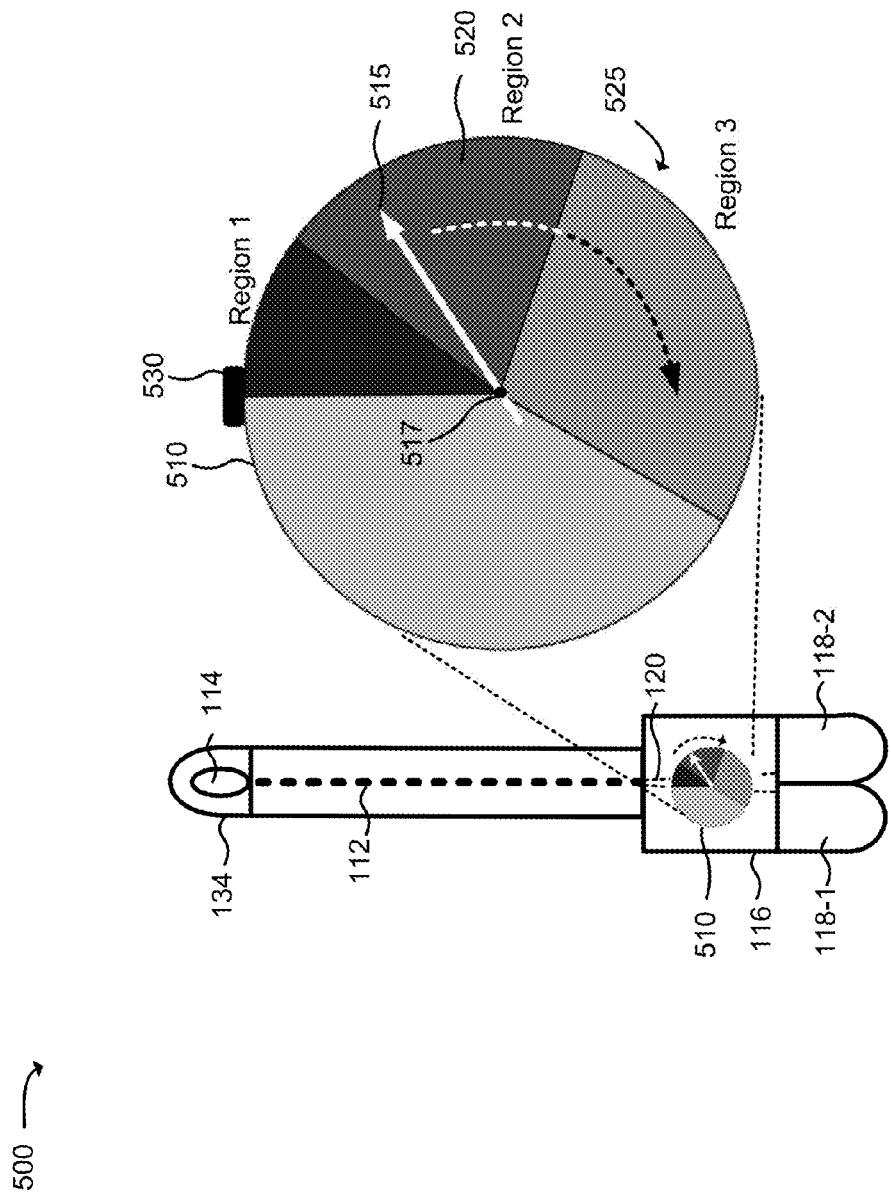

FIGS. 5A-5C are diagrams of example test devices that may be used to analyze a sample, obtained from a patient, for the presence and/or severity of a bacterial infection. Any of the test devices of FIGS. 5A-5C or other test devices may be used to perform process 300 of FIG. 3. FIG. 5A is a diagram of a test device 500 used to obtain a sample from a patient and to analyze the sample for the presence and/or severity of a bacterial infection. Test device 500 may include a collection of components described above in connection with FIGS. 1B and 1C, such as tube component 112, swab 114, handle 116, reservoirs 118-1 and 118-2, channel 120, cylinder 132, and test chamber 134, as well as timer component 510.

Timer 510 may include a timer hand 515, a timer face 520, a timer module 525 and a switch 530. Timer hand 515 may represent a rigid material, such as a rod, beam, etc. that is attached at or near a first end by shaft 517. Shaft 517 may represent a rigid material, such as a rod, that is approximately perpendicular to timer hand 515 and may attached to timer module 525 at a first end and to timer hand 515 at a second end. The second end of timer hand 515 may represent a pointing device similar to a hand on a clock. Timer face 520 may include a time scale that is similar to the time scale on horizontal axis 410 of FIG. 4. Additionally, or alternatively, timer face 520 may include one or more regions each of which correspond to the time frames (e.g., regions 1-3) described above with respect to FIG. 4. Timing module 525 (not shown in FIG. 5A) may represent a simple mechanical and/or electrical timer that starts or stops each time switch 530 is actuated (e.g., by depressing, etc). Thus, when switch 530 is actuated, timing module 525 may start, which may cause shaft 517 to begin to rotate. The rotation of shaft 517 may cause timer hand 515 to rotate. Actuating switch 530 again may cause timing module 525 to stop thereby causing shaft 517 and/or timer hand 515 to stop rotating. Switch 530 may be actuated by an operator (e.g., a medical doctor, a nurse, a physician's assistant, or some other medical practitioner). Additionally, or alternatively, switch 530 may be integrated into timer 510 in a manner that causes switch 530 to be actuated when sample device 110 is inserted into test module 130 and/or is removed from test module 130.

By way of example, when sample device 110 is inserted into test module 130, swab 114, on which a sample has been taken, may perforate and/or may be inserted into test chamber 134. The insertion of swab 114 into test chamber 134 may cause a second reagent to be applied to the sample, which may trigger a bacterial indication mechanism if bacterial cells are included within the sample. Additionally, or alternatively, switch 530 may be actuated (e.g., when cylinder 132 makes contact with switch 530), which may cause the timer module 525 to start and timer hand 515 to begin to rotate. If a positive indication is detected within test chamber 134 when timer hand 515 is located within region 1, the operator may determine that the sample includes bacterial cells and/or that the bacterial population within the sample corresponds to a first level of severity of a bacterial infection (e.g., a high level of severity). If a positive indication is detected within test chamber 134 when timer hand 515 is located within region 2, the operator may determine that the sample includes bacterial cells and/or that the bacterial population within the sample corresponds to a second level of severity of a bacterial infection (e.g., a medium level of severity) that is less than the first level of bacterial infection. If a positive indication is detected within test chamber 134 when timer hand 515 is located within region 3, the operator may determine that the sample includes bacterial cells and/or that the bacterial population within the sample corresponds to a third level of severity of a bacterial infection (e.g., a low level of severity) that is less than the second level of bacterial infection. If a positive indication is not detected within the one or more regions (e.g., within regions 1-3), the operator may determine that the sample does not include bacterial cells and/or corresponds to a bacterial population that is less than a threshold.

FIG. 5B is a diagram of a test device 550 used to analyze a sample, obtained from a patient, for the presence and/or severity of a bacterial infection. Test device 550 may include a collection of components such as a swab 555, a pair of reservoirs 560-1 and 560-2 (hereinafter referred to collectively as "reservoirs 560" and individually as "reservoir 560"), and a test chamber 562. Swab 555 may represent a conventional swap with which a sample can be obtained from a patient. Reservoir 560 may include a chamber that securely stores a one or more first reagent solutions (e.g., described above with respect to FIG. 2A) to preserve shelf life, to permit portability or storage of test device 550, etc. Additionally, or alternatively, reservoir 560 may be made of a suitable material (e.g., plastic, etc.) that can be penetrated by swab 555 when an operator mechanically perforates reservoir 555 with swab 555 and/or inserts swab 555 into reservoir 555. Test Chamber 562 may include a chamber that stores one or more second reagent solutions (e.g., as described above with respect to FIG. 2B) to preserve shelf life, permit portability or storage of test device 550, etc. Additionally, or alternatively, test chamber 562 may be made of a suitable material (e.g., a transparent plastic or some other transparent material) that can be penetrated by swab 555 when an operator mechanically perforates test chamber 562 with swab 555 and/or inserts swab 555 into test chamber 562, and which permits the operator to observe whether the one or more second reagent solutions change in appearance when swab 555 is inserted into test chamber 562. Reservoirs 560 and test chamber 562 may, in one example, be arranged and/or aligned adjacent to each other in a manner that permits the operator to insert swab 555 into and remove swab 555 from each reservoir 560 before being inserted into test chamber 562.

By way of example, the operator may insert swab 555 into reservoir 560-1 (e.g., as shown by indication A) that stores a first reagent solution (e.g., as described above with respect to FIG. 2A) to cause background ATP to be released from somatic cells and/or to hydrolyze the released background ATP for effective removal from the sample. The operator may remove swab 555 from reservoir 560-1 and may insert swab 555 into reservoir 560-2 (e.g., as shown by indication B) that stores a different first reagent solution (e.g., as described above with respect to FIG. 2A) to cause ATP to be release from bacterial cells within the sample, if the sample includes bacterial cells. The operator may remove swab 555 from reservoir 560-2 and may insert swab 555 into test chamber 562 (e.g., as shown by indication C) that stores a second reagent solution (e.g., as described above with respect to FIG. 2B) to trigger a bacterial indication mechanism within test chamber 562 (if the sample includes bacterial cells) in a manner similar to that described above with respect to FIG. 2B. The operator may observe the second reagent solution within test chamber 562 to determine whether a positive indication can be detected using the unaided eye.

FIG. 5C is a diagram of a test device 575 used to analyze a sample, obtained from a patient, for the presence and/or severity of a bacterial infection. Test device 575 may include the collection of components as described above with respect to FIG. 5B, such as swab 555, reservoirs 560, and test chamber 562. Reservoirs 560 and test chamber 562 may, in one example, be arranged and/or aligned in a manner that is different from that described above with respect to FIG. 5B. For example, reservoirs 560 and test chamber 562 may be adjacent to each other in a longitudinal arrangement that resembles, for example, a cylindrical configuration about an axis adjacent. This configuration may permit the operator to insert swab 555 into each reservoir and test chamber without first removing swab 555 from each of reservoirs 560 or test chamber 562.

By way of example, the operator may insert swab 555 into reservoir 560-1 (e.g., as shown by indication A) that stores the first reagent solution (e.g., as described above with respect to FIG. 2A) to cause background ATP to be released from somatic cells and/or to hydrolyze the released background ATP for effective removal from the sample. The operator may cause swab 555 to be further inserted into test device 575 until swab 555 is inserted into reservoir 560-2 (e.g., as shown by indication B) that stores the different first reagent solution (e.g., as described above with respect to FIG. 2A) to cause ATP to be release from bacterial cells within the sample, if the sample includes bacterial cells. The operator may further insert swab 555 into test device 575 until swab 555 is inserted into test chamber 562 (e.g., as shown by indication C) that stores the second reagent solution (e.g., as described above with respect to FIG. 2B) to trigger the bacterial indication mechanism within test chamber 562 (if the sample includes bacterial cells) in a manner similar to that described above with respect to FIG. 2B. The operator may observe the second reagent solution within test chamber 562 to determine whether a positive indication can be detected using the unaided eye.

The quantity of devices and/or components, associated with test devices 500, 550, and 575 of FIGS. 5A, 5B, and 5C, respectively, are identified for explanatory purposes only. In practice, test devices 500, 550, and/or 575 may include additional devices and/or components; fewer devices and/or components; different devices and/or components; or differently arranged devices and/or components than illustrated in FIGS. 5A-5C.

FIGS. 6A and 6B are diagrams of test device 600 used to obtain a sample from a patient and to automatically analyze the sample for the presence and/or severity of a bacterial infection. As illustrated in FIG. 6A, test device 600 may include a collection of components described above in connection with FIG. 1B, such as tube component 112, swab 114, handle 116, reservoirs 118-1 and 118-2, and channel 120. Test device 600 may also include a test module 610.

Test module 610 may include a cylinder 615, a test chamber 620, a sample analyzer 625, and a display 630. Cylinder 615 may represent a hollow cylinder with a first end that is open to permit the insertion of tube 112 and swab 114 and a second end to which test chamber 620 is attached. Cylinder 615 may also, or alternatively, be made of a material that is sufficiently rigid to maintain shape; to permit sample analyzer 625 and/or display 630 to be mounted; to permit repeated insertion and/or removal of tube 112 and swab 114; and/or to be repeatedly fastened to, or unfastened from, sample device 110. Test chamber 620 may store one or more second reagent solutions (e.g., reagent 3), as described above with respect to FIG. 2B. Additionally, or alternatively, test chamber 620 may be made of a suitable material that enables swab 114 (e.g., that includes the sample and the first reagents from sample device 110) to perforate and enter test chamber 620 when the full length of tube 112 and swab 114 are inserted (e.g., fully inserted) into test module 610 as illustrated in FIG. 6B. Additionally, or alternatively, all or part of test chamber 620 may be made of a material that is optically transparent such that a sensor, associated with sample analyzer 625, can observe a change in appearance (e.g., a positive indication due to a change in color, pattern, texture, etc.) of a second reagent within test chamber 620.

Sample analyzer 625, to be described in greater detail below with respect to FIG. 7, may perform one or more operations to determine whether a sample includes cells associated with a bacterial infection and/or to identify a level of severity associated with such a bacterial infection. Sample analyzer 625 may, for example, monitor test chamber 620 to detect whether a positive indication is created within test chamber 620. Sample analyzer 625 may also, or alternatively, automatically initiate an operation to analyze the sample when sample device 110 is inserted into test module 610 and one or more second reagents (e.g., reagent 3) are applied to the sample when swab 114 perforates and/or enters test chamber 620. Display 630 may include a display medium on which sample analyzer 625 presents information for display. Display 630 may, for example, include a liquid crystal display (e.g., LCD), a light emitting diode (LED) display, a plasma display, a line display, etc. Display 630 may display a notification, received from sample analyzer 625, indicating whether a bacterial infection is detected within the sample. Display module 630 may also, or alternatively, display a notification, received from sample analyzer 625, indicating a level of severity of a bacterial infection.

The quantity of devices and/or components, associated with test device 600, is provided for explanatory purposes only. In practice, test device 600 may include additional devices and/or components; fewer devices and/or components; different devices and/or components; or differently arranged devices and/or components than illustrated in FIG. 6. Alternatively, or additionally, one or more of the devices and/or components of test device 600 may perform one or more functions described as being performed by another one or more of the devices and/or components of test device 600.

FIG. 7 is a diagram of example devices of sample analyzer 625. As shown in FIG. 7, sample analyzer 625 may include a controller 710, a switch 715, a detector 720, and a storage 725. The quantity of devices, illustrated in FIG. 7, is provided for explanatory purposes only. In practice, there may be additional devices; fewer devices; different devices; or differently arranged devices than illustrated in FIG. 7. Alternatively, or additionally, one or more of the devices of sample analyzer 625 may perform one or more functions described as being performed by another one or more of the devices of sample analyzer 625.

Controller 710 may include one or more computation and communication devices that gather, process, search, store, and/or provide information in a manner described herein. Controller 710 may also include one or more devices that are capable of communicating with switch 715, detector 720, display 630, and/or storage 725. Controller 710 may, for example, receive a signal from switch 715 that indicates that an operation to analyze is a sample is to be initiated. Controller 710 may, based on receiving the notification, cause detector 720 to begin monitoring test chamber 620 and may receive a signal from detector 720 indicator whether a positive indication is detected. Controller 710 may determine a time associated with performing the analysis and may communicate with storage 725 to perform a look up operation to determine whether a bacterial infection is detected and/or a level of severity associated with the bacterial infection. Controller 710 may present information, for display, to display 630 that indicates whether a bacterial infection is detected and/or that identifies a level of severity associated with the bacterial infection.

Switch 715 may include one or more devices that is capable of providing a signal or stop providing a signal to controller 710 based on an input. Switch 715 may include a contact that, when closed connects switch 715 to a power source (e.g., a battery, an alternating current source, etc.) and which permits power flow to controller 710. When the contact is open, switch 715 may not be connected to the power source, which precludes an electrical signal from the battery from being provided to controller 710. The contact may be closed when test chamber 620 is perforated by swab 114; when cylinder 615 makes contact and/or is connected to handle 116; when test chamber 620 is compressed (e.g., by a medical doctor, a nurse, a physician's assistant, or some other medical practitioner); etc.

Detector 720 may include one or more components that are capable monitoring an appearance associated with test chamber 620. Detector 720 may, for example, include a camera, a photo detector, photo diodes, phototransistors, reversed-bias LEDs, etc. Detector 720 may receive an optical signal (e.g., in the visual spectrum, infrared spectrum, ultraviolet spectrum, or some combination thereof) from test chamber 620 based on an appearance associated with test chamber 620. Detector 720 may output a signal (e.g., an electrical signal, an optical signal, etc.) to controller 710 that is based on the received optical signal.

Storage 725 may include one or more devices that store information used by controller 710 to perform operations described herein. Storage 725 may, for example, store information used to determine whether a bacterial infection is detected and/or a level of severity of the bacterial infection based on a period of time. Storage 725 may also, or alternatively, store a lookup table that associates relative levels of severity of a bacterial infection detected within a sample and/or a relative bacterial population of the sample with periods of time associated with an operation performed by controller 710.

Figure 8:
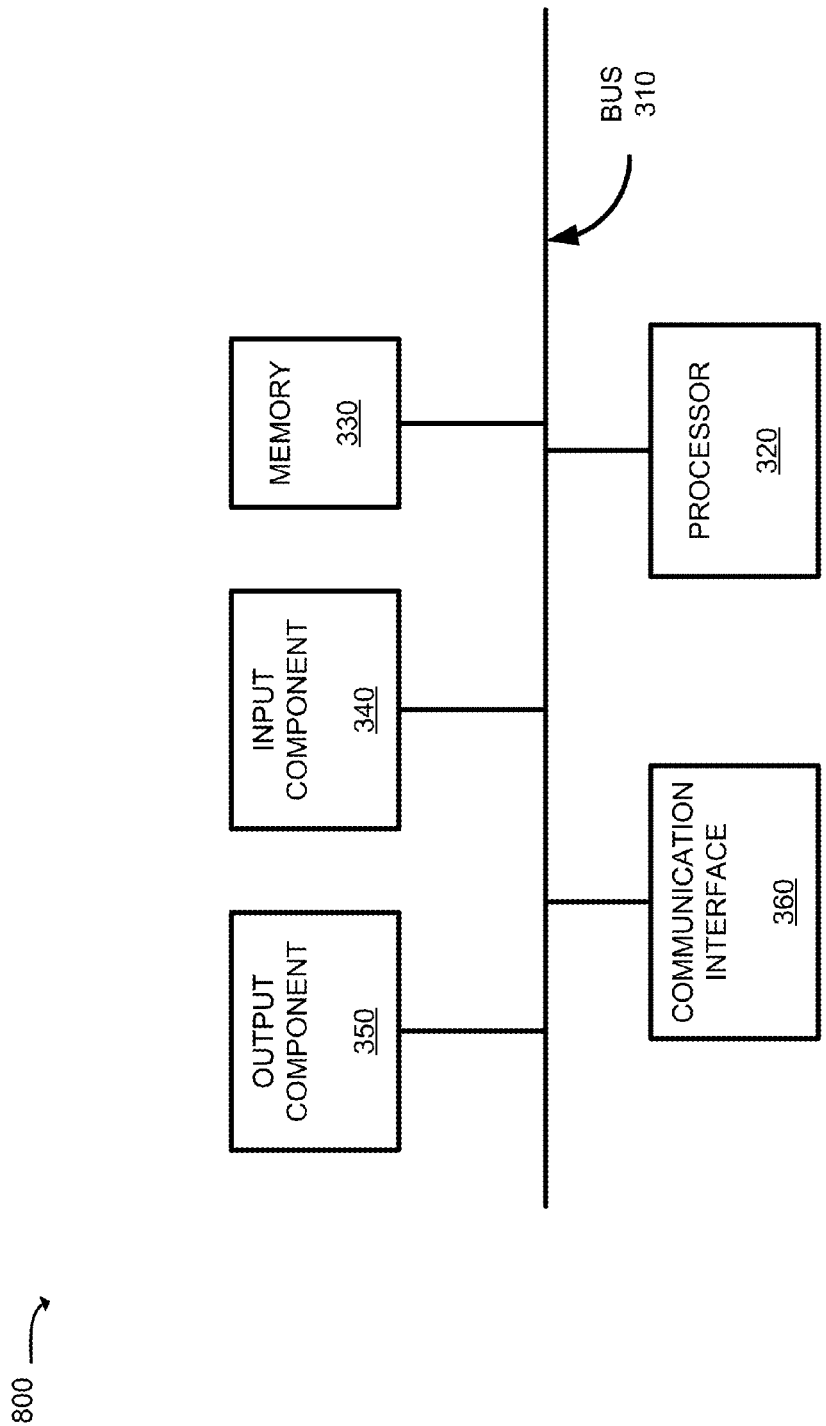
FIG. 8 is a diagram of example components a controller component of FIG. 7.

FIG. 8 is a diagram of example components of a device 800. Device 800 may correspond to controller 710. Alternatively, or additionally, controller 710 may include one or more devices 800 and/or one or more components of device 800.

Device 800 may include a bus 810, a processor 820, a memory 830, an input component 840, an output component 850, and a communication interface 860. Although FIG. 8 shows example components of device 800, in other implementations, device 800 may contain fewer components, additional components, different components, or differently arranged components than depicted in FIG. 8. For example, device 800 may include one or more switch fabrics instead of, or in addition to, bus 810. Additionally, or alternatively, one or more components of device 800 may perform one or more tasks described as being performed by one or more other components of device 800.

Bus 810 may include a path that permits communication among the components of device 800. Processor 820 may include a processor, a microprocessor, or processing logic that may interpret and execute instructions. Memory 830 may include any type of dynamic storage device that may store information and instructions, for execution by processor 820, and/or any type of non-volatile storage device that may store information for use by processor 820.

Input component 840 may include a mechanism that permits a user to input information to device 800, such as a keyboard, a keypad, a button, a switch, etc. Output component 850 may include a mechanism that outputs information to the user, such as a display, a speaker, one or more light emitting diodes (LEDs), etc. Communication interface 860 may include any transceiver-like mechanism that enables device 800 to communicate with other devices and/or systems via wireless communications, wired communications, or a combination of wireless and wired communications. For example, communication interface 860 may include mechanisms for communicating with another device or system via a network. Alternatively, or additionally, communication interface 860 may be a logical component that includes input and output ports, input and output systems, and/or other input and output components that facilitate the transmission of data to other devices.

Device 800 may perform certain operations in response to processing unit 820 executing software instructions contained in a computer-readable medium, such as memory 830. A computer-readable medium may be defined as a non-transitory memory device. A memory device may include space within a single physical memory device or spread across multiple physical memory devices. The software instructions may be read into memory 830 from another computer-readable medium or from another device. The software instructions contained in memory 830 may cause processor 820 to perform processes described herein. Alternatively, hardwired circuitry may be used in place of or in combination with software instructions to implement processes described herein. Thus, implementations described herein are not limited to any specific combination of hardware circuitry and software.

Although FIG. 8 shows example components of device 800, in other implementations, device 800 may include fewer components, different components, differently arranged components, or additional components than depicted in FIG. 8. Alternatively, or additionally, one or more components of device 800 may perform one or more other tasks described as being performed by one or more other components of device 800.

Figure 10B:
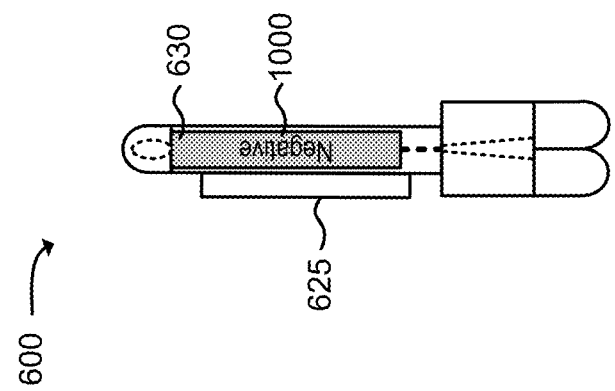
FIGS. 10A-10D are diagrams of a test device displaying example test results of an analysis of a sample.
Figure 10A:
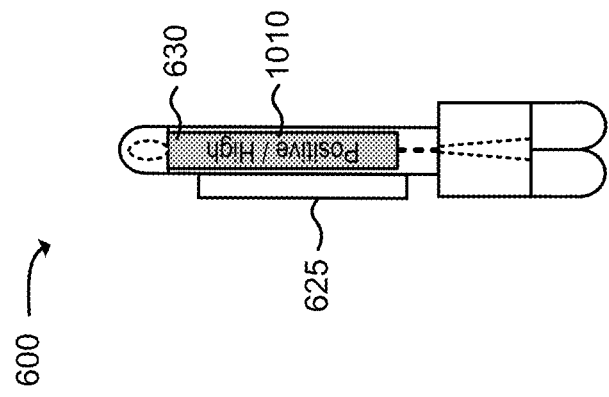

FIG. 9 is a flow chart of an example process 900 for determining the presence and/or severity of a bacterial infection within a sample taken from a patient. In an example implementation, process 900 may be performed by test device 600 of FIG. 6. Additionally, or alternatively, process 900 may be performed by a device or collection of devices separate from, or in combination with, test device 600 of FIG. 6. FIGS. 10A-10D are diagrams of test device 600 displaying test results 1000-1030, respectively, of an analysis of a sample. FIG. 11 is a diagram of a data structure 1100 that may store information associated with determining bacterial infection severity. All or a portion of process 900 of FIG. 9 will be described below with references to example test results 1000-1030 of FIGS. 10A-10D, respectively, and data structure 1100 of FIG. 11.

Assume, in the description below and in a manner similar to that described above with respect to blocks 305-310 of FIG. 3, that a sample has been obtained from a patient (e.g., using sample device 110, or a swab, etc.), and that one or more first reagents (e.g., reagent 1 of FIG. 2A) have been applied to the sample to remove background ATP, extracted from somatic cells within the sample, from the sample. Assume further, and in a manner similar to that described with respect to block 315 of FIG. 3, that another one or more first reagents (e.g., reagent 2 of FIG. 2A) has been applied to the sample thereby causing ATP to be released from any bacterial cells that may exist within the sample.

As shown in FIG. 9, process 900 may include receiving an instruction to analyze a sample (block 905) and begin monitoring the sample based on receiving the instruction (block 910). For example, an operator (e.g., a medical doctor, a nurse, a physician's assistant, or some other medical practitioner) may instruct test device 600 to begin analyzing a sample by inserting sample device 110 (e.g., tube 112 and swab 114), which includes a sample obtained from the patient, into test module 610 thereby causing swab 114 to perforate and/or enter test chamber 620 in which a second reagent is stored (e.g., reagent 3 of FIG. 2B). More particularly, test device 600 (e.g., switch 715) may detect when swab 114 enters test chamber 620, cylinder 615 makes contact with and/or is connected to handle 116, when test chamber 620 is compressed (e.g., by a medical doctor, a nurse, a physician's assistant, or some other medical practitioner), and/or when an operator presses a button associated with test device 600 (e.g., switch 715). The detection, for example, may occur when switch 715 sends a signal to controller 710.

When the instruction is received, test device 600 may initiate an operation to analyze the sample. For example, test device 600 (e.g., detector 720) may begin monitoring the sample based on the detection of sample device 110 being inserted into test module 610. Test device 600 may store, in a memory associated with test device 600 (e.g., storage 725 or some other memory), a time at which the detection occurred and/or monitoring the sample begins. Additionally, or alternatively, test device 600 may present, for display (e.g., on display 630), a notification indicating that the sample is being tested (e.g., "Testing").

As also shown in FIG. 9, if a visual indication is not detected (block 915—NO), process 900 may include identifying a first time period associated with monitoring the sample (block 920) and identifying a time threshold (block 925). For example, test device 600 may, based on monitoring the sample, determine whether a positive indication can be detected. Test device 600 may, for example, determine that the second reagent within test chamber 620 has not changed in appearance. Based on the determination that the second reagent has not changed in appearance, test device 600 may determine that a positive indication has not been detected.

Test device 600 (e.g., controller 710) may identify a first time period associated with the operation to analyze the sample. The first time period may, for example, be based on a difference between a current time (e.g., a time at which test device 600 determines that a positive indication is not detected) and the first time at which the detection occurred and/or test device 600 began monitoring the sample. Test device 600 may also, or alternatively, identify a time threshold that is predetermined by test device 600. In one example, test device 600 may retrieve the time threshold from a memory associated with test device 600 (e.g., storage 725 and/or some other memory).

As further shown in FIG. 9, if the first time period is greater than the time threshold (block 930—YES), process 900 may include presenting, for display, a notification that the sample does not include a bacterial infection (block 935). For example, test device 600 (e.g., controller 710) may compare the first time period to the time threshold to determine that the first time period is greater than the time threshold. When the first time period is greater than the time threshold, test device 600 may present, for display (e.g., on display 630), a notification that a bacterial infection is not detected within the sample. For example, as illustrated in FIG. 10A, display 630 may depict notification 1000 (e.g., shown as "Negative") that corresponds to a negative indication when a change in appearance of the second reagent is not detected within the first time period that is greater than the time threshold. The operator may use the negative indication to determine that antibiotics are not to be prescribed for the patient from which the sample was obtained.

As still further shown in FIG. 9, if the first time period is not greater than the time threshold (block 930—NO), process 900 may include monitoring the sample based on receiving the instruction (block 910). For example, test device 600 (e.g., controller 710) may, based on the comparison of the first time period to the time threshold, determine that the first time period is not greater than the time threshold. When the first time period is not greater than the time threshold, test device 600 may continue to monitor the sample in a manner similar to that described above with respect to block 910. In one example, test device 600 may continue to present, for display (e.g., on display 630), a notification indicating that the sample is being tested (e.g., "Testing").

As also shown in FIG. 9, if the visual indication is detected (block 915—YES), process 900 may include presenting for display, a notification that the sample includes a bacterial infection (block 940). For example, test device 600 may, based on monitoring the sample, determine that a positive indication is detected. Test device 600 may, in this example, determine that the second reagent within test chamber 620 has changed in appearance (e.g., has changed in color, pattern, texture, etc.). Based on the determination that the second reagent has changed in appearance, test device 600 (e.g., controller 710) may determine that a positive indication has been detected. Based on detecting the positive indication, test device 600 may present, for display (e.g., on display 630), a notification that a positive indication has been detected (e.g., "Positive"), which may indicate that bacterial cells are included within the sample.

As further shown in FIG. 9, process 900 may include identifying a second time period associated with detecting the visual indication (block 945) and determining a level of severity associated with the bacterial infection based on the second time period (block 950). Test device 600 (e.g., controller 710) may identify a second time period associated with the operation to analyze the sample. The second time period may, for example, be based on a difference between a current time (e.g., a time at which test device 600 detects the positive indication) and the first time at which test device 600 began monitoring the sample via test chamber 620.

Additionally, or alternatively, test device 600 may determine a level of severity, associated with the bacterial infection, based on the second time period. In one example, test device 600 may use the second time period to perform a lookup operation to determine the level of severity. In this example, test device 600 may access a data structure, such as data structure 1100 of FIG. 11, to identify a level of severity, associated with the bacterial infection, based on the second time.

As illustrated in FIG. 11, data structure 1100 may include a time period field 1105, a severity level field 1110, and a bacterial population field 1115. In an example implementation, data structure 1100 may be stored within storage 725. Data structure 1100 includes fields 1105-1115 for explanatory purposes. In another implementation, data structure 1100 may include additional fields, fewer fields, different fields, or differently arranged fields than are depicted in FIG. 11.

Time period field 1105 may store information that identifies a period of time associated with detecting a positive indication within a particular sample. Severity level field 1110 may store information that identifies a relative level of severity, associated with a bacterial infection that is included within the particular sample, based on the time period identified in time period field 1105. Bacterial population field 1115 may store information that identifies a bacterial population within the particular sample that corresponds to the level of severity identified in severity field 1110.

Thus, by way of example, test device 600 may determine that the second time period most closely matches a time period identified within the data structure (e.g., shown as Tp1 with respect to ellipse 1117 of FIG. 11). Based on the time period identified within the data structure, test device 600 may determine that a relative severity level of the bacterial infection corresponds to a first severity level (e.g., shown as High by ellipse 1117). Additionally, or alternatively, based on the identification of the first severity level and/or the time period, test device 600 may determine a first bacterial population (e.g., shown as "P1" by ellipse 1117) associated with of the bacterial infection within the sample.

Additionally, or alternatively, test device 600 may determine that the second time period most closely matches a particular time period identified within the data structure (e.g., shown as Tpa by ellipse 1119 of FIG. 11). The particular time period may be greater than the time period. Based on the particular time period, test device 600 may determine that a relative severity level of the bacterial infection corresponds to a second severity level (e.g., shown as Medium by ellipse 1119). The second severity level may be less than the first severity level. Additionally, or alternatively, based on the identification of the second severity level and/or the particular time period, test device 600 may determine a second bacterial population (e.g., shown as "Pa" by ellipse 1119) associated with of the bacterial infection within the sample. The second bacterial population may be less than the first bacterial population.

Additionally, or alternatively, test device 600 may determine that the second time period most closely matches a different time period identified within the data structure (e.g., shown as Tpx by ellipse 1121 of FIG. 11). The different time period may be greater than the particular time period. Based on the different time period, test device 600 may determine that a relative severity level of the bacterial infection corresponds to a third severity level (e.g., shown as Low by ellipse 1121). The third severity level may be less than the second severity level. Additionally, or alternatively, based on the identification of the third severity level and/or the different time period, test device 600 may determine a third bacterial population (e.g., shown as "Px" by ellipse 1121) associated with of the bacterial infection within the sample. The third bacterial population may be less than the second bacterial population.

As yet further shown in FIG. 9, process 900 may include presenting, for display, a notification indicating that a level of severity associated with the bacterial infection (block 955). For example, based on the level of severity of the bacterial infection, test device 600 may present, for display (e.g., on display 630), results of the test via a notification that indicates that a positive indication has been detected. The notification may also, or alternatively, include an indication a severity level of the bacterial infection and/or a bacterial population associated with the sample. For example, as shown in FIG. 10B, when the first severity level is determined, test device 600 may display notification 1010 which identifies the positive indication and the first severity level (e.g., shown as "Positive/High" in FIG. 10B). Additionally, or alternatively, notification may include other information (not shown in FIG. 10B) that identifies the first bacterial population (e.g., P1) that corresponds to the first severity level.

Figure 10C:
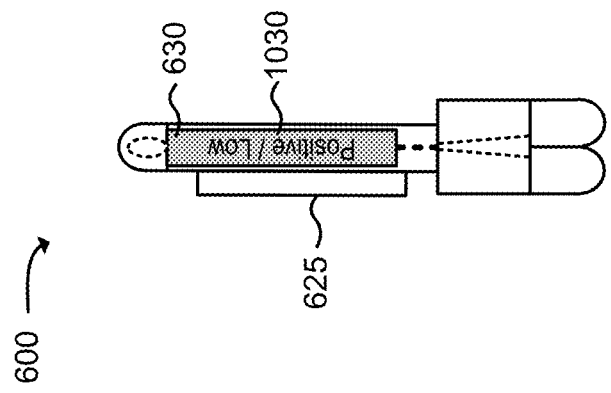
Figure 10D:
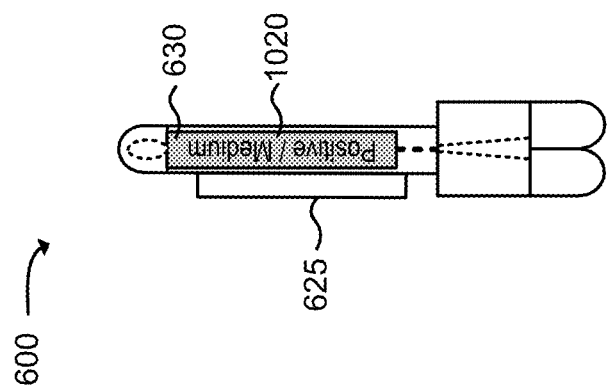
Figure 11:
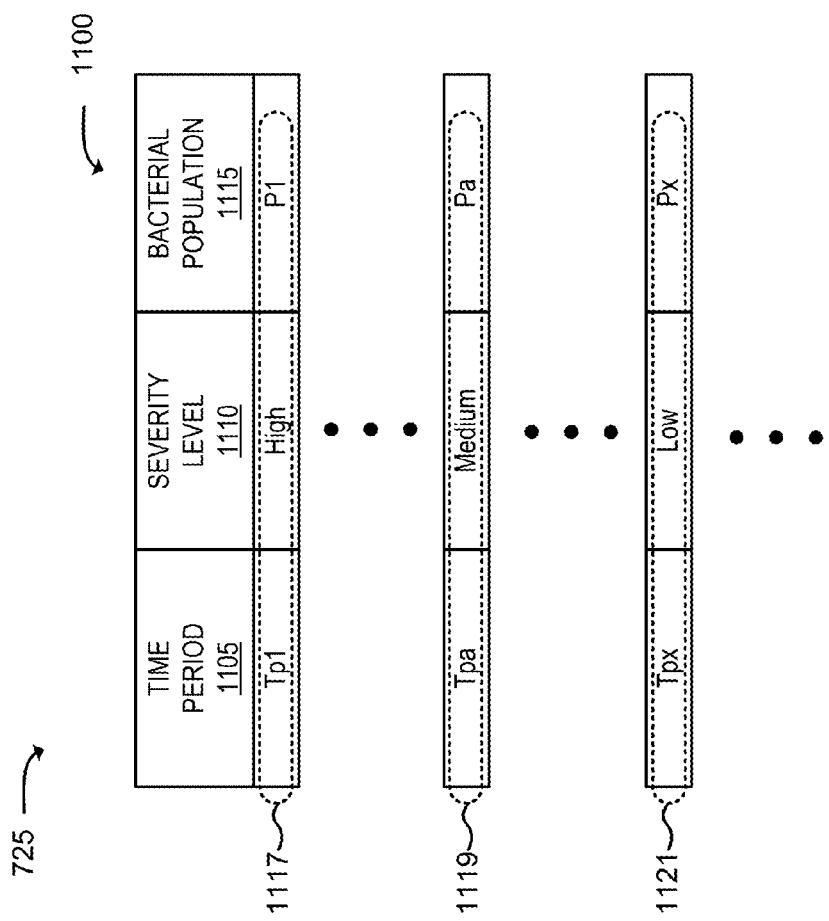
FIG. 11 is a diagram of a data structure that may store information associated with bacterial infection severity.

Additionally, or alternatively, as shown in FIG. 10C, when the second severity level is determined, test device 600 may display notification 1020 which identifies the positive indication and the second severity level (e.g., shown as "Positive/Medium" in FIG. 10C). Additionally, or alternatively, the notification may include other information (not shown in FIG. 10C) that identifies the second bacterial population (e.g., Pa) that corresponds to the second severity level. Additionally, or alternatively, as shown in FIG. 10D, when the third severity level is determined, test device 600 may display notification 1030 which identifies the positive indication and the third severity level (e.g., shown as "Positive/Low" in FIG. 10D). Additionally, or alternatively, the notification may include other information (not shown in FIG. 10D) that identifies the third bacterial population (e.g., Px) that corresponds to the third severity level.

The notification of the positive indication and the relative severity level (e.g., as shown by FIGS. 10B-10D), may enable the operator to determine that the patient may be suffering from a bacterial infection and a relative severity level of such a bacterial infection. The notification may also assist the operator in prescribing antibiotics and/or for determining a dosage that is most effective based on the severity level and/or the bacterial population.

Technologies and/or techniques, described herein, may enable a test device to determine whether a patient is suffering from a bacterial infection or a non-bacterial infection (e.g., a viral infection). The technologies and/or techniques may enable the test device to be used, by an operator (e.g., a medical doctor, a nurse, a physician's assistant, or some other medical practitioner), to obtain a sample from the patient and to analyze the sample for the presence of a bacterial infection. The technologies and/or techniques may enable reagents to be applied to the sample, which may cause, within a short period of time (e.g., within 1 minutes, 5 minutes, 10 minutes, etc.), a positive indication to be detected when a bacterial infection is present within the sample or a negative indication to be detected when the bacterial infection is not present within the sample. The positive indication or negative indication may be discernable to the unaided eye without the aid of a sensing or an amplifying device distinct from the test device.

The technologies and/or techniques may enable the test device to identify a time at which a positive indication is detected and may determine a relative level of severity of the bacterial infection or a bacterial population within the sample based on the identified time. The technologies and/or techniques may enable the operator to determine, within the short period of time associated with the point of care (e.g., during the patient's visit to the medical facility), whether to prescribe antibiotics based on whether a positive indication or negative indication is detected. The test device may also, or alternatively, aid the practitioner in determining dosage levels of the antibiotics based on the level of severity and/or the bacterial population of the bacterial infection within the sample. The technologies and/or techniques may reduce health care costs and the amount of time associated with performing laboratory tests (e.g., sending samples to remote laboratories for testing, growing cultures, etc.) to determine whether an infection is bacterial or non-bacterial and may mitigate the problem associated with over-prescribing antibiotics as a remedy when patients are not suffering from a bacterial infection.

The foregoing description provides illustration and description, but is not intended to be exhaustive or to limit the implementations to the precise form disclosed. Modifications and variations are possible in light of the above disclosure or may be acquired from practice of the embodiments.

While series of blocks have been described with regard to FIGS. 3 and 9, the order of the blocks may be modified in other implementations. Further, non-dependent blocks may be performed in parallel.

It will be apparent that systems and methods, as described above, may be implemented in many different forms of software, firmware, and hardware in the implementations illustrated in the figures. The actual software code or specialized control hardware used to implement these systems and methods is not limiting of the embodiments. Thus, the operation and behavior of the systems and methods were described without reference to the specific software code—it being understood that software and control hardware can be designed to implement the systems and methods based on the description herein.

Further, certain portions, described above, may be implemented as a component that performs one or more functions. A component, as used herein, may include hardware, such as a processor, an application specific integrated circuit (ASIC), or a field programmable gate array (FPGA), or a combination of hardware and software (e.g., a processor executing software).

It should be emphasized that the terms "comprises"/ "comprising" when used in this specification are taken to specify the presence of stated features, integers, steps or components but does not preclude the presence or addition of one or more other features, integers, steps, components or groups thereof.

Even though particular combinations of features are recited in the claims and/or disclosed in the specification, these combinations are not intended to limit the disclosure of the embodiments. In fact, many of these features may be combined in ways not specifically recited in the claims and/or disclosed in the specification. Although each dependent claim listed below may directly depend on only one other claim, the disclosure of the embodiments includes each dependent claim in combination with every other claim in the claim set.

No element, act, or instruction used in the present application should be construed as critical or essential to the embodiments unless explicitly described as such. Also, as used herein, the articles "a" and "an" are intended to include one or more items and may be used interchangeably with "one or more." Where only one item is intended, the term "one" or similar language is used. Further, the phrase "based on" is intended to mean "based, at least in part, on" unless explicitly stated otherwise.

What is claimed is:

1. A method for determining whether a sample, obtained from a patient, includes a bacterial infection, the method comprising:
    obtaining, from the patient, the sample that includes a plurality of cells of the patient;
    applying, to the sample, one or more first reagents to cause adenosine triphosphate (ATP) to be released from bacterial cells, when the plurality of cells include the bacterial cells;
    applying, to the sample, a second reagent, in liquid form, to react with the ATP that is released from the bacterial cells, when the plurality of cells include the bacterial cells, the reaction with the ATP forming a colorimetric agent that can be detected by an unaided eye of a medical practitioner;
    determining whether the colorimetric agent is detected by the unaided eye of the medical practitioner;
    identifying a time period from when the second reagent is applied to when the colorimetric agent is detected by the unaided eye of the medical practitioner; and
    determining that the patient:
        has the bacterial infection when the time period, from when the second reagent is applied to when the colorimetric agent is detected by the unaided eye of the medical practitioner, is less than a threshold, the threshold corresponding to a duration of a point of care office visit between the patient and the medical practitioner, or
        does not have the bacterial infection when the time period, from when the second reagent is applied to when the colorimetric agent is detected by the unaided eye of the medical practitioner, is not less than the threshold.

2. The method of claim 1, where the duration of the point of care office visit is less than or approximately equal to 30 minutes.

3. The method of claim 1 further comprising:
    determining that the patient does not have the bacterial infection when the colorimetric agent is not detected by the unaided eye of the medical practitioner.

4. The method of claim 1, where the change in appearance can be detected by the medical practitioner without using a sensing device or an amplifying device.

5. The method of claim 1, where the colorimetric indicator corresponds to a reduction of formazane dye that occurs when the second reagent reacts with the ATP.

6. The method of claim 1, where determining the level of severity of the bacterial infection further includes:
    determining whether the time period is greater than a first threshold,
    determining that the level of severity of the bacterial infection corresponds to:
        a first level of severity when the time period is not greater than the first threshold, and
        a second level of severity when the time period is greater than the first threshold, the second level of severity being less than the first level of severity.

7. The method of claim 1, further comprising:
    detecting the colorimetric agent, after applying the second reagent to the sample, when the sample has changed from at least one of:
        a first color to a second color, the first color being different than the second color;
        a first pattern to a second pattern, the first pattern being different than the second pattern; or
        a first texture to a second texture, the first texture being different than the second texture.

8. The method of claim 1, where applying the one or more first reagents further comprises:

applying, to the sample, a first reagent, of the one or more first reagents, to cause background ATP to be released from somatic cells, of the plurality of cells, associated with the patient; and applying, to the sample, a different first reagent, of the one or more first reagents, to cause the background ATP to be removed from the sample.

9. A method for performing an assay on a sample from a patient to detect a bacterial infection or a severity level of the bacterial infection, the method comprising:

obtaining, from the patient, the sample that includes a plurality of cells of the patient;

applying, to the sample, one or more first reagents to cause adenosine triphosphate (ATP) to be released from bacterial cells when the sample includes the bacterial cells;

applying, to the sample, a second reagent in liquid form to cause the second reagent to react with the released ATP when the sample includes the bacterial cells, the reaction forming a colorimetric agent having a concentration that is based on a quantity of the released ATP;

detecting whether the sample has changed in appearance, the change in appearance being detected by an unaided eye of a medical practitioner when the concentration of the colorimetric agent is greater than a threshold;

identifying a time period from when the second reagent is applied to the sample to when the change in appearance is detected; and determining a level of severity, of the bacterial infection, based on the time period, from when the second reagent is applied to the sample to when the change in appearance is detected, the level of severity corresponding to at least one of:

a first level of severity when the time period is less than a duration of a point of care visit by a first amount, a second level of severity, that is more severe than the first level of severity, when the time period is less than the duration of the point of care visit by a second amount, the second amount being greater than the first amount, or a third level of severity, that corresponds to an absence of the bacterial infection, when the time period is not less than the duration of the point of care visit.

10. The method of claim 9 where the duration of the point of care visit is less than or approximately equal to thirty minutes.

11. The method of claim 9, where the first level of severity corresponds to a first quantity of the bacterial cells and the second level of severity corresponds to a second quantity of the bacterial cells, the first quantity of bacterial cells being less than the second quantity of bacterial cells.

12. The method of claim 9, where the colorimetric agent corresponds to a reduction of formazane dye that occurs when the second reagent reacts with the ATP.

13. The method of claim 9, where a quantity of the ATP is approximately equal to zero when the sample does not include the bacterial cells, or where the concentration of the colorimetric agent is approximately equal to zero when the quantity of the ATP is approximately equal to zero.

14. The method of claim 9 where when applying the one or more first reagents further comprises:

applying, to the sample, a first reagent, of the one or more first reagents, to:

cause background ATP to be release from somatic cells, of the plurality of cells, within the sample, and hydrolyze the released background ATP to cause the background ATP to be removed from or become inert within the sample; and applying, to the sample and after applying the particular reagent, a different first reagent, of the one or more first reagents, to cause the ATP to be released from the bacterial cells when the sample includes the bacterial cells.

15. A method for determining a level of severity of a bacterial infection within a sample obtained from a patient, the method comprising:

receiving the sample;

applying, to the sample, a first reagent to release and remove background adenosine triphosphate (ATP) from the sample when the sample includes somatic cells of the patient;

applying, to the sample, a second reagent to release ATP from bacterial cells of the patient when the sample includes the bacterial cells;

applying, to the sample, a third reagent to react with the released ATP to form a colorimetric agent when the sample includes the bacterial cells monitoring, the sample, to detect whether the colorimetric agent causes the reagent to change in appearance;

detecting that the reagent has changed in appearance, the change in appearance being detected by an unaided eye of an observer or without using a luminometer or optical amplification device;

identifying a time period from a first time when the third reagent is applied to the sample to a second time when the reagent changing in appearance is detected; and determining a level of severity, of the bacterial infection, based on the time period, from a first time when the third reagent is applied to the sample to a second time when the reagent changing in appearance is detected, the level of severity corresponding to at least one of:

a first level of severity when the time period is less than a threshold by a first amount, the threshold being associated with a typical duration of a point of care visit between the patient and a medical practitioner, a second level of severity when the time period is less than the threshold by an amount that is less than the first amount, the second level of severity being less severe than the first level of severity, or a third level of severity, when the time period is not less than the threshold, the third level of severity indicating that the sample does not include the bacterial infection.

16. The method of claim 15, where the typical duration of the point of care visit is less than or approximately equal to thirty minutes.

17. The method of claim 15, where the first reagent includes at least one of:

a first constituent agent that causes somatic cell membranes to become permeable to the background ATP, which enables the background ATP to be released from the somatic cells; or a second constituent agent that hydrolyzes or binds the released background ATP to render the background ATP inert, inactive, and/or effectively removed from the sample.

18. The method of claim 15, where the second reagent includes at least one of:

a first constituent agent to cause bacterial cell membranes, associated with the bacterial cells, to become permeable to ATP to enable the ATP to be released from the bacterial cells when the sample includes the bacterial cells.

19. The method of claim 15, where the third reagent includes at least one of:
   hexokinase,
   glucose,
   magnesium sulfate heptahydrate,
   glucose 6 phosphate dehydrogenase,
   nicotinamide adenine dinucleotide (NAD),
   diaphorase,
   formazane dye, or
   a buffer.

20. The method of claim 15, where the third reagent includes at least one of:
   hexokinase within a range of 0.5 percent to 2.0 percent of the third reagent by volume at approximately 125 enzyme units per milligram,
   glucose within a range of 2.0 percent to 10.0 percent of the third reagent by volume,
   magnesium sulfate heptahydrate within a range of 2.0 percent to 6.0 percent of the third reagent by volume at approximately 2.0 moles per liter (M),
   glucose 6 phosphate dehydrogenase within a range of 0.1 percent to 0.6 percent of the third reagent by volume at approximately 450 enzyme units per milligram,
   nicotinamide adenine dinucleotide (NAD) within a range of 5.0 percent to 10.0 percent of the third reagent by volume,
   diaphorase within a range of 0.5 percent to 3.0 percent of the third reagent by volume at approximately 100 enzyme units per milligram,
   formazane dye within a range of approximately 6.0 percent to approximately 15.0 percent of the reagent by volume, or
   a buffer within a range of approximately 30.0 percent to approximately 50.0 percent of the third reagent by volume at approximately 2.0 moles per liter.

21. The method of claim 20, where the reagent includes at least one of:
   phosphofructokinase or glucose dehydrogenase as a substitute for the hexokinase,
   lactose as a substitute for the glucose,
   magnesium hexahydrate as a substitute for the magnesium sulfate heptahydrate,
   lactate dehydrogenase as a substitute for the glucose 6 phosphate dehydrogenase,
   flavin adenine dinucleotide as a substitute for the nicotinamide adenine dinucleotide (NAD),
   glutathione reductase or lipoyl dehydrogenase as a substitute for the diaphorase, or
   resazurin as a substitute for the formazane dye.

22. The method of claim 15, where the colorimetric agent corresponds to a reduced formazane dye.

* * * * *